(12) United States Patent
Jacobs et al.

(10) Patent No.: US 8,278,419 B2
(45) Date of Patent: Oct. 2, 2012

(54) FIBRONECTIN TYPE III DOMAIN BASED SCAFFOLD COMPOSITIONS, METHODS AND USES

(75) Inventors: Steven Jacobs, Radnor, PA (US); Karyn O'Neil, Radnor, PA (US)

(73) Assignee: Centocor Ortho Biotech Inc., Horsham, PA (US)

( * ) Notice: Subject to any disclaimer, the term of this patent is extended or adjusted under 35 U.S.C. 154(b) by 170 days.

(21) Appl. No.: 12/606,382

(22) Filed: Oct. 27, 2009

(65) Prior Publication Data

US 2010/0216708 A1    Aug. 26, 2010

Related U.S. Application Data

(60) Provisional application No. 61/110,120, filed on Oct. 31, 2008.

(51) Int. Cl.
     *C07K 14/00*      (2006.01)
     *C07K 17/00*      (2006.01)

(52) U.S. Cl. ........................................ 530/353; 530/402

(58) Field of Classification Search .................... None
See application file for complete search history.

(56) References Cited

U.S. PATENT DOCUMENTS

| | | | |
|---|---|---|---|
| 6,018,030 A | 1/2000 | Ferrari et al. | |
| 6,355,776 B1 | 3/2002 | Ferrari et al. | |
| 6,462,189 B1 | 10/2002 | Koide | |
| 6,673,901 B2 | 1/2004 | Koide | |
| 6,703,199 B1 | 3/2004 | Koide | |
| 6,818,418 B1 | 11/2004 | Lipovsek | |
| 6,846,655 B1 | 1/2005 | Wagner et al. | |
| 7,078,490 B2 | 7/2006 | Koide | |
| 7,115,396 B2 | 10/2006 | Lipovsek | |
| 7,119,171 B2 | 10/2006 | Koide | |
| 7,153,661 B2 | 12/2006 | Koide | |
| 2004/0259781 A1 | 12/2004 | Chiquet-Ehrismann et al. | |
| 2005/0255548 A1 | 11/2005 | Lipovsek et al. | |
| 2006/0040278 A1 | 2/2006 | Cojocaru et al. | |
| 2006/0246059 A1 | 11/2006 | Lipovsek et al. | |
| 2006/0270604 A1 | 11/2006 | Lipovsek et al. | |
| 2007/0148126 A1 | 6/2007 | Chen et al. | |
| 2007/0160533 A1 | 7/2007 | Chen et al. | |
| 2007/0184476 A1 | 8/2007 | Hsieh et al. | |
| 2008/0015339 A1 | 1/2008 | Lipovsek et al. | |
| 2008/0220049 A1 | 9/2008 | Chen et al. | |

FOREIGN PATENT DOCUMENTS

| | | |
|---|---|---|
| EP | 1 137 941 B1 | 12/1998 |
| EP | 0 985 039 B1 | 3/2000 |
| EP | 1 266 025 B1 | 12/2002 |
| WO | WO 01/64942 A1 | 9/2001 |
| WO | WO 2004/029224 A2 | 4/2004 |
| WO | WO 2004/058821 A2 | 7/2004 |
| WO | WO 2007/085815 A2 | 8/2007 |
| WO | WO 2008/156642 A1 | 12/2008 |

OTHER PUBLICATIONS

Helms et al. Destabilizing loop swaps in the CDRs of an immunoglobulin VL domain. Protein Science 4:2073-2081, 1995.*
Reiss et al. Inhibition of platelet aggregation by grafting RGD and KGD sequences on the structural scaffold of small disulfide-rich proteins. Platelets 17(3):153-157, 2006.*
Koivunen et al. Identification of Receptor Ligands with Phage Display Peptide Libraries J Nucl Med; 40:883-888, 1999.*
Kuntz. Structure-based strategies for drug design and discovery. Science. 1992 257(5073):1078-1082.*
Miller et al Ligand binding to proteins: the binding landscape model. Protein Sci. Oct. 1997;6(10):2166-79.*
Attwood TK. Genomics. The Babel of bioinformatics. Science. 290(5491):471-473, 2000.*
Skolnick et al. From genes to protein structure and function: novel applications of computational approaches in the genomic era. Trends Biotechnol. 18(1):34-9, 2000.*
Siggers et al. Conformational dynamics in loop swap mutants of homologous fibronectin type III domains. Biophys J. Oct. 1, 2007;93(7):2447-56.*
PCT International Search Report dated Jul. 15, 2010.
Dutta, et al., "High-affinity fragment complementation of a fibronectin type III domain and its application to stability enhancement," Protein Science, 14: 2838-2848 (2005).
Binz, et al., "Engineered proteins as specific binding reagents," Current Opinion in Biotechnology, 16:459-469 (2005).
Skerra, et al., "Engineered protein scaffolds for molecular recognition," Journal of Molecular Recognition, 13: 167-187 (2000).
Koide, et al., "The Fibronectin Type III Domain as a Scaffold for Novel Binding Proteins," Journal of Molecular Biology, 284: 1141-1151 (1998).
Karatan, et al., "Molecular Recognition Properties of FN3 Monobodies that Bind the Src SH3 Domain," Chemistry & Biology, 11:835-844 (2004).
Parker, et al., "Antibody mimics based on human fibronectin type three domain engineered for thermostability and high-affinity binding to vascular endothelial growth factor receptor two," Protein Engineering, Design & Selection, 18(9):435-444 (2005).
Lehmann, et al., "Engineering proteins for thermostability: the use of sequence alignments versus rational design and directed evolution," Current Opinions in Biotechnology, 12: 371-375 (2001).

* cited by examiner

*Primary Examiner* — Maher Haddad
(74) *Attorney, Agent, or Firm* — Eric Dichter

(57) ABSTRACT

A protein scaffold based on a consensus sequence of fibronectin type III (FN3) proteins, such as the tenth FN3 repeat from human fibronectin (human Tenascin), including isolated nucleic acids that encode a protein scaffold, vectors, host cells, and methods of making and using thereof have applications in diagnostic and/or therapeutic compositions, methods and devices. In particular, protein scaffold molecules binding to IgG have been identified as useful for diagnostic and/or therapeutic applications.

1 Claim, 7 Drawing Sheets

FIBRONECTIN TYPE III DOMAIN BASED SCAFFOLD COMPOSITIONS, METHODS AND USES

CROSS-REFERENCE TO RELATED APPLICATIONS

This application claims priority to U.S. Provisional Application Ser. No. 61/110,120 filed 31 Oct. 2008, the entire contents of which is incorporated herein by reference in its entirety.

FIELD OF THE INVENTION

The present invention relates to protein scaffolds with novel properties, including the ability to bind to cellular targets. More particularly, the present invention is directed to a protein scaffold based on a consensus sequence of a fibronectin type III (FN3) repeat.

BACKGROUND OF THE INVENTION

Monoclonal antibodies are the most widely used class of therapeutic proteins when high affinity and specificity for a target molecule are desired. However, non-antibody proteins that can be engineered to bind such targets are also of high interest in the biopharmaceutical industry. These "alternative scaffold" proteins may have advantages over traditional antibodies due to their small size, lack of disulphide bonds, high stability, and ability to be expressed in prokaryotic hosts. Novel methods of purification are readily applied; they are easily conjugated to drugs/toxins, penetrate efficiently into tissues and are readily formatted into multispecific binders (Skerra 2000; Binz and Pluckthun 2005).

One such alternative scaffold is the immunoglobulin (Ig) fold. This fold is found in the variable regions of antibodies, as well as thousands of non-antibody proteins. It has been shown that one such Ig protein, the tenth fibronectin type III (FN3) repeat from human fibronectin, can tolerate a number of mutations in surface exposed loops while retaining the overall Ig-fold structure. Thus, libraries of amino acid variants have been built into these loops and specific binders selected to a number of different targets (Koide et al. 1998; Karatan et al. 2004). Such engineered FN3 domains have been found to bind to targets with high affinity, while retaining important biophysical properties (Parker et al. 2005).

Desirable physical properties of potential alternative scaffold molecules include high thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase α-helix propensity, engineering of salt bridges, alteration of the surface charge of the protein, directed evolution, and composition of consensus sequences (Lehmann and Wyss 2001). High thermal stability is a desired property of such scaffolds as it may increase the yield of recombinant protein obtained, improve solubility of the purified molecule, improve activity of intracellular scaffolds, decrease immunogenicity, and minimize the need of a cold chain in manufacturing.

SUMMARY OF THE INVENTION

The present invention provides a protein scaffold based on a fibronectin type III (FN3) repeat protein, encoding or complementary nucleic acids, vectors, host cells, compositions, combinations, formulations, devices, and methods of making and using them. In a preferred embodiment, the protein scaffold is comprised of a consensus sequence of multiple FN3 domains from human Tenascin-C (hereinafter "Tenascin"). In a further preferred embodiment, the protein scaffold of the present invention is a consensus sequence of 15 FN3 domains. The protein scaffolds of the invention can be designed to bind various molecules, for example, a cellular target protein.

The protein scaffolds of the invention may include additional molecules or moieties, for example, the Fc region of an antibody, albumin binding domain, or other moiety influencing half-life. In further embodiments, the protein scaffolds of the invention may be bound to a nucleic acid molecule that may encode the protein scaffold.

The present invention also provides at least one method for expressing at least one protein scaffold based on a consensus sequence of multiple FN3 domains, in a host cell, comprising culturing a host cell as described herein under conditions wherein at least one protein scaffold is expressed in detectable and/or recoverable amounts.

The present invention also provides at least one composition comprising (a) a protein scaffold based on a consensus sequence of multiple FN3 domains and/or encoding nucleic acid as described herein; and (b) a suitable and/or pharmaceutically acceptable carrier or diluent.

The present invention further comprises a method of generating libraries of a protein scaffold based on a fibronectin type III (FN3) repeat protein, preferably, a consensus sequence of multiple FN3 domains and, more preferably, a consensus sequence of multiple FN3 domains from human Tenascin. The library is formed by making successive generations of scaffolds by altering (by mutation) the amino acids or the number of amino acids in the molecules in particular positions in portions of the scaffold, e.g., loop regions. Libraries can be generated by altering the amino acid composition of a single loop or the simultaneous alteration of multiple loops or additional positions of the scaffold molecule. The loops that are altered can be lengthened or shortened accordingly. Such libraries can be generated to include all possible amino acids at each position, or a designed subset of amino acids. The library members can be used for screening by display, such as in vitro display (DNA, RNA, ribosome display, etc.), yeast, bacterial, and phage display.

The protein scaffolds of the present invention provides enhanced biophysical properties, such as stability under reducing conditions and solubility at high concentrations; they may be expressed and folded in prokaryotic systems, such as E. coli, in eukaryotic systems, such as yeast, and in in vitro transcription/translation systems, such as the rabbit reticulocyte lysate system In an additional aspect, the present invention provides a method of generating a scaffold molecule that binds to a particular target by panning the scaffold library of the invention with the target and detecting binders. In other related aspects, the invention comprises screening methods that may be used to generate or affinity mature protein scaffolds with the desired activity, e.g., capable of binding to target proteins with a certain affinity. Affinity maturation can be accomplished by iterative rounds of mutagenesis and selection using systems, such as phage display or in vitro display. Mutagenesis during this process may be the result of site directed mutagenesis to specific scaffold residues, random mutagenesis due to error-prone PCR, DNA shuffling, and/or a combination of these techniques. The present invention further provides any invention described herein.

DESCRIPTION OF THE INVENTION

The present invention provides an isolated, recombinant and/or synthetic protein scaffold based on a consensus sequence of fibronectin type III (FN3) repeat protein, including, without limitation, mammalian-derived scaffold, as well as compositions and encoding nucleic acid molecules comprising at least one polynucleotide encoding protein scaffold based on the consensus FN3 sequence. The present invention further includes, but is not limited to, methods of making and using such nucleic acids and protein scaffolds, including diagnostic and therapeutic compositions, methods and devices.

The protein scaffolds of the present invention offer advantages over conventional therapeutics, such as ability to administer locally, orally, or cross the blood-brain barrier, ability to express in *E. Coli* allowing for increased expression of protein as a function of resources versus mammalian cell expression ability to be engineered into bispecific molecules that bind to multiple targets or multiple epitopes of the same target, ability to be conjugated to drugs, polymers, and probes, ability to be formulated to high concentrations, and the ability of such molecules to effectively penetrate diseased tissues and tumors.

Moreover, the protein scaffolds possess many of the properties of antibodies in relation to their fold that mimics the variable region of an antibody. This orientation enables the FN3 loops to be exposed similar to antibody complementarity determining regions (CDRs). They should be able to bind to cellular targets and the loops can be altered, e.g., affinity matured, to improve certain binding or related properties.

Figure 6:
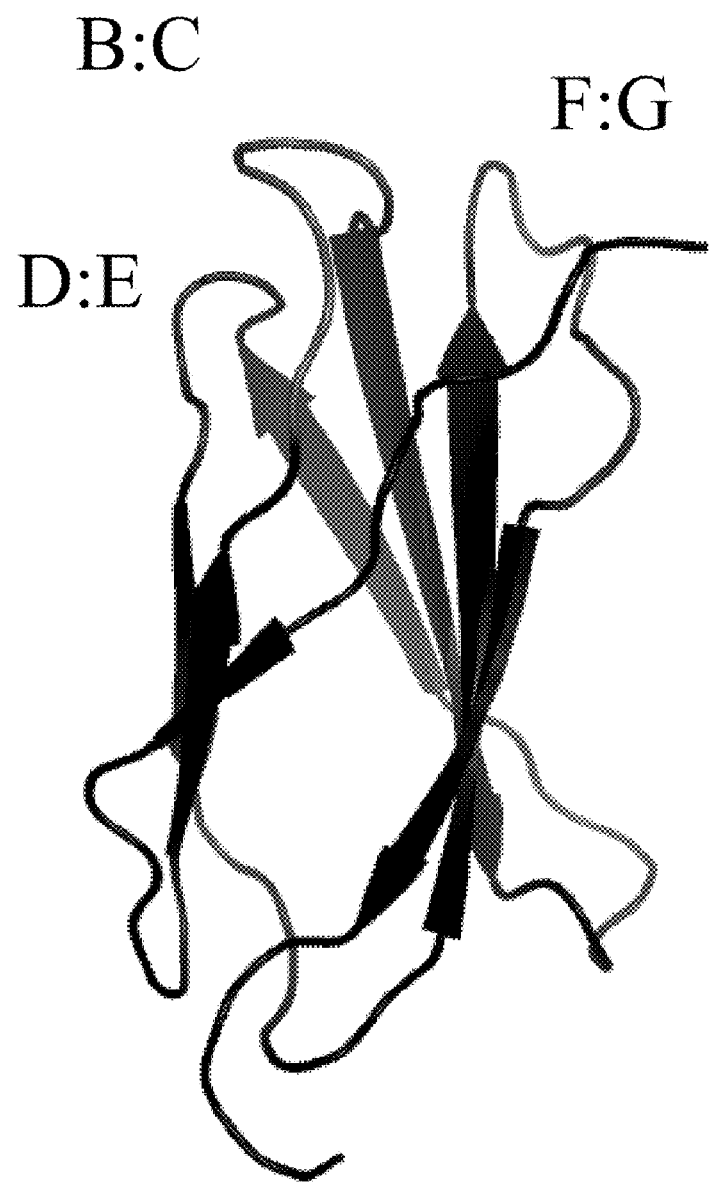
FIG. 6. Loop structure of the $3^{rd}$ FN3 domain of human Tenascin.

Three of the six loops of the protein scaffold of the invention correspond topologically to the complementarity determining regions (CDRs 1-3), i.e., antigen-binding regions, of an antibody, while the remaining three loops are surface exposed in a manner similar to antibody CDRs. These loops span at or about residues 13-16, 22-28, 38-43, 51-54, 60-64, and 75-81 of SEQ ID NO:16 as shown in Table 3 below and FIG. 6. Preferably, the loop regions at or about residues 22-28, 51-54, and 75-81 are altered for binding specificity and affinity. One or more of these loop regions are randomized with other loop regions and/or other strands maintaining their sequence as backbone portions to populate a library and potent binders can be selected from the library having high affinity for a particular protein target. One or more of the loop regions can interact with a target protein similar to an antibody CDR interaction with the protein.

The scaffolds of the present invention may incorporate other subunits, e.g., via covalent interaction. All or a portion of an antibody constant region may be attached to the scaffold to impart antibody-like properties, e.g., complement activity (ADCC), half-life, etc. For example, effector function can be provided and/or controlled, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., protein scaffold loops) and can be assessed using various assays (e.g., Fc binding assays, ADCC assays, CDC assays, etc.).

Additionally, a toxin conjugate, albumin or albumin binders, polyethylene glycol (PEG) molecules may be attached to the scaffold molecule for desired properties. Any of these fusions may be generated by standard techniques, for example, by expression of the fusion protein from a recombinant fusion gene constructed using publicly available gene sequences.

The scaffolds of the present invention can be used as monospecific in monomeric form or as bi- or multi-specific (for different protein targets or epitopes on the same protein target) in multimer form. The attachments may be covalent or non-covalent. For example, a dimeric bispecific scaffold has one subunit with specificity for a first target protein or epitope and a second subunit with specificity for a second target protein or epitope. Scaffold subunits can be joined in a variety of conformations that can increase the valency and thus the avidity of antigen binding.

As used herein, an "antibody" includes any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof. Such antibody optionally further affects a specific ligand, such as but not limited to, where such antibody modulates, decreases, increases, antagonizes, agonizes, mitigates, alleviates, blocks, inhibits, abrogates and/or interferes with at least one activity or binding, or with receptor activity or binding, in vitro, in situ and/or in vivo.

The term "antibody" is further intended to encompass antibodies, digestion fragments, specified portions and variants thereof, including, without limitation, antibody mimetics or comprising portions of antibodies that mimic the structure and/or function of an antibody or specified fragment or portion thereof, including, without limitation, single chain antibodies, single domain antibodies, and fragments thereof. Functional fragments include antigen-binding fragments that bind to a particular target. For example, antibody fragments capable of binding to a particular target or portions thereof, including, but not limited to, Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the CH$_1$ domain and/or hinge region of the heavy chain. The various portions of antibodies can be joined together chemically by conventional techniques, or can be prepared as a contiguous protein using genetic engineering techniques.

A scaffold protein of the present invention can be used to measure or effect in a cell, tissue, organ or animal (including mammals and humans), to diagnose, monitor, modulate, treat, alleviate, help prevent the incidence of, or reduce the symptoms of, at least one disease or condition, selected from, but not limited to, at least one of an immune disorder or disease, a cardiovascular disorder or disease, an infectious, malignant, and/or neurologic disorder or disease, or other known or specified related condition.

Such a method can comprise administering an effective amount of a composition or a pharmaceutical composition comprising at least one scaffold protein to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 μg/ml serum concentration per single, multiple, or continuous administration, or any effective range or value therein, as done and determined using known methods, as described herein or known in the relevant arts.

Scaffold Protein of the Present Invention—Production and Generation

At least one scaffold protein of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2$^{nd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

Amino acids from a scaffold protein can be altered, added and/or deleted to reduce immunogenicity or reduce, enhance or modify binding, affinity, on-rate, off-rate, avidity, specificity, half-life, stability, solubility or any other suitable characteristic, as known in the art.

Optionally, scaffold proteins can be engineered with retention of high affinity for the antigen and other favorable biological properties. To achieve this goal, the scaffold proteins can be optionally prepared by a process of analysis of the parental sequences and various conceptual engineered products using three-dimensional models of the parental and engineered sequences. Three-dimensional models are commonly available and are familiar to those skilled in the art. Computer programs are available which illustrate and display probable three-dimensional conformational structures of selected candidate sequences and can measure possible immunogenicity (e.g., Immunofilter program of Xencor, Inc. of Monrovia, Calif.). Inspection of these displays permits analysis of the likely role of the residues in the functioning of the candidate sequence, i.e., the analysis of residues that influence the ability of the candidate scaffold protein to bind its antigen. In this way, residues can be selected and combined from the parent and reference sequences so that the desired characteristic, such as affinity for the target antigen(s), is achieved. Alternatively, or in addition to, the above procedures, other suitable methods of engineering can be used.

Screening

Screening protein scaffolds for specific binding to similar proteins or fragments can be conveniently achieved using nucleotide (DNA or RNA display) or peptide display libraries, for example, in vitro display. This method involves the screening of large collections of peptides for individual members having the desired function or structure. The displayed nucleotide or peptide sequences can be from 3 to 5000 or more nucleotides or amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278.

Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge Antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5856456, assigned to Enzon; 5,223,409, 5,403,484, 5,571, 698, 5,837,500, assigned to Dyax, 5,427,908, 5,580,717, assigned to Affymax; 5,885,793, assigned to Cambridge Antibody Technologies; 5,750,373, assigned to Genentech, 5,618,920, 5,595,898, 5,576,195, 5,698,435, 5,693,493, 5,698,417, assigned to Xoma, Colligan, supra; Ausubel, supra; or Sambrook, supra.

The protein scaffolds of the invention can bind human or other mammalian proteins with a wide range of affinities ($K_D$). In a preferred embodiment, at least one protein scaffold of the present invention can optionally bind to a target protein with high affinity, for example, with a $K_D$ equal to or less than about $10^{-7}$ M, such as but not limited to, 0.1-9.9 (or any range or value therein) X $10^{-8}$, $10^{-9}$, $10^{-10}$, $10^{-11}$, $10^{-12}$, $10^{-13}$, $10^{-14}$, $10^{-15}$ or any range or value therein, as determined by surface plasmon resonance or the Kinexa method, as practiced by those of skill in the art.

The affinity or avidity of a protein scaffold for an antigen can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W.H. Freeman and Company: New York, N.Y. (1992); and methods described herein). The measured affinity of a particular protein scaffold-antigen interaction can vary if measured under different conditions (e.g., salt concentration, pH). Thus, measurements of affinity and other antigen-binding parameters (e.g., $K_D$, $K_{on}$, $K_{off}$) are preferably made with standardized solutions of protein scaffold and antigen, and a standardized buffer, such as the buffer described herein.

Competitive assays can be performed with the protein scaffold of the present invention in order to determine what proteins, antibodies, and other antagonists compete for binding to a target protein with the protein scaffold of the present invention and/or share the epitope region. These assays as readily known to those of ordinary skill in the art evaluate competition between antagonists or ligands for a limited number of binding sites on a protein. The protein and/or antibody is immobilized or insolubilized before or after the competition and the sample bound to the target protein is separated from the unbound sample, for example, by decanting (where the protein/antibody was preinsolubilized) or by centrifuging (where the protein/antibody was precipitated after the competitive reaction). Also, the competitive binding may be determined by whether function is altered by the binding or lack of binding of the protein scaffold to the target protein, e.g., whether the protein scaffold molecule inhibits or potentiates the enzymatic activity of, for example, a label. ELISA and other functional assays may be used, as well known in the art.

Nucleic Acid Molecules

Nucleic acid molecules of the present invention encoding protein scaffolds can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally, with one or more introns, e.g., but not limited to, at least one specified portion of at least one protein scaffold; nucleic acid molecules comprising the coding sequence for a protein scaffold or loop region that binds to the target protein; and nucleic acid molecules which comprise a nucleotide sequence substantially different from those described above but which, due to the degeneracy of the genetic code, still encode the protein scaffold as described herein and/or as known in the art. Of course, the genetic code is well known in the art. Thus, it would be routine for one skilled in the art to generate such degenerate nucleic acid variants that code for specific protein scaffolds of the present invention. See, e.g., Ausubel, et al., supra, and such nucleic acid variants are included in the present invention.

As indicated herein, nucleic acid molecules of the present invention which comprise a nucleic acid encoding a protein scaffold can include, but are not limited to, those encoding the amino acid sequence of a protein scaffold fragment, by itself; the coding sequence for the entire protein scaffold or a portion thereof; the coding sequence for a protein scaffold, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding a protein scaffold can be fused to a marker sequence, such as a sequence encoding a peptide that facilitates purification of the fused protein scaffold comprising a protein scaffold fragment or portion.

Polynucleotides Selectively Hybridizing to a Polynucleotide as Described Herein

The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of a protein scaffold encoded by the polynucleotides described herein. The polynucleotides of this invention embrace nucleic acid sequences that can be employed for selective hybridization to a polynucleotide encoding a protein scaffold of the present invention. See, e.g., Ausubel, supra; Colligan, supra, each entirely incorporated herein by reference.

Construction of Nucleic Acids

The isolated nucleic acids of the present invention can be made using (a) recombinant methods, (b) synthetic techniques, (c) purification techniques, and/or (d) combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries are well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; 5,142,033 to Innis; 5,122,464 to Wilson, et al.; 5,091,310 to Innis; 5,066,584 to Gyllensten, et al; 4,889,818 to Gelfand, et al; 4,994,370 to Silver, et al; 4,766,067 to Biswas; 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention further provides recombinant expression cassettes comprising a nucleic acid of the present invention. A nucleic acid sequence of the present invention, for example, a cDNA or a genomic sequence encoding a protein scaffold of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in the intron) of a non-heterologous form of a polynucleotide of the present invention so as to up or down regulate expression of a polynucleotide of the present invention. For example, endogenous promoters can be altered in vivo or in vitro by mutation, deletion and/or substitution.

Vectors and Host Cells

The present invention also relates to vectors that include isolated nucleic acid molecules of the present invention, host cells that are genetically engineered with the recombinant vectors, and the production of at least one protein scaffold by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, methotrexate (MTX), dihydrofolate reductase (DHFR, U.S. Pat. Nos. 4,399,216; 4,634,665; 4,656,134;

4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one protein scaffold of the present invention can be expressed in a modified form, such as a fusion protein, and can include not only secretion signals, but also additional heterologous functional regions. For instance, a region of additional amino acids, particularly charged amino acids, can be added to the N-terminus of a protein scaffold to improve stability and persistence in the host cell, during purification, or during subsequent handling and storage. Also, peptide moieties can be added to a protein scaffold of the present invention to facilitate purification. Such regions can be removed prior to final preparation of a protein scaffold or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the present invention. Alternatively, nucleic acids of the present invention can be expressed in a host cell by turning on (by manipulation) in a host cell that contains endogenous DNA encoding a protein scaffold of the present invention. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the protein scaffolds, specified portions or variants thereof, are bacterial, yeast, and mammalian cells as known in the art. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or an SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of a Protein Scaffold

A protein scaffold can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Protein scaffolds of the present invention include naturally purified products, products of chemical synthetic procedures, and products produced by recombinant techniques from a prokaryotic or eukaryotic host, including, for example, *E. Coli*, yeast, higher plant, insect and mammalian cells. Depending upon the host employed in a recombinant production procedure, the protein scaffold of the present invention can be glycosylated or can be non-glycosylated. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Amino Acid Codes

The amino acids that make up protein scaffolds of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994). A protein scaffold of the present invention can include one or more amino acid substitutions, deletions or additions, either from natural mutations or human manipulation, as specified herein. Amino acids in a protein scaffold of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one neutralizing activity. Sites that are critical for protein scaffold binding can also be identified by structural analysis, such as crystallization, nuclear magnetic resonance or photoaffinity labeling (Smith, et al., J. Mol. Biol. 224:899-904 (1992) and de Vos, et al., Science 255:306-312 (1992)).

As those of skill will appreciate, the present invention includes at least one biologically active protein scaffold of the present invention. Biologically active protein scaffolds have a specific activity at least 20%, 30%, or 40%, and, preferably, at least 50%, 60%, or 70%, and, most preferably, at least 80%, 90%, or 95%-1000% or more of that of the native (non-synthetic), endogenous or related and known protein scaffold. Methods of assaying and quantifying measures of enzymatic activity and substrate specificity are well known to those of skill in the art.

In another aspect, the invention relates to protein scaffolds and fragments, as described herein, which are modified by the covalent attachment of an organic moiety. Such modification can produce a protein scaffold fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified protein scaffolds and fragments of the invention can comprise one or more organic moieties that are covalently bonded, directly or indirectly, to the antibody. Each organic moiety that is bonded to a protein scaffold or fragment of the invention can independently be a hydrophilic polymeric group, a fatty acid group or a fatty acid ester group. As used herein, the term "fatty acid" encompasses monocarboxylic acids and di-carboxylic acids. A "hydrophilic polymeric group," as the term is used herein, refers to an organic polymer that is more soluble in water than in octane. For example, polylysine is more soluble in water than in octane. Thus, a protein scaffold modified by the covalent attachment of polylysine is encompassed by the invention. Hydrophilic polymers suitable for modifying protein scaffolds of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the protein scaffold of the invention has a molecular weight of about 800 to about 150,000 Daltons as a separate molecular entity. For example, $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying protein scaffolds of the invention can be saturated or can contain one or more units of unsaturation. Fatty acids that are suitable for modifying protein scaffolds of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-$\Delta$9-octadecanoate ($C_{18}$, oleate), all cis-$\Delta$5,8,11,14-eicosatetraenoate ($C_{20}$, arachidonate), octanedioic acid, tetradecanedioic acid, octadecanedioic acid, docosanedioic acid, and the like. Suitable fatty acid esters include monoesters of dicarboxylic acids that comprise a linear or branched lower alkyl group. The lower alkyl group can comprise from one to about twelve, preferably, one to about six, carbon atoms.

The modified protein scaffolds and fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example, a divalent $C_1$-$C_{12}$ group wherein one or more carbon atoms can be replaced by a heteroatom, such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate, as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified protein scaffolds of the invention can be produced by reacting a protein scaffold or fragment with a modifying agent. For example, the organic moieties can be bonded to the protein scaffold in a non-site specific manner by employing an amine-reactive modifying agent, for example, an NHS ester of PEG. Modified protein scaffolds and fragments comprising an organic moiety that is bonded to specific sites of a protein scaffold of the present invention can be prepared using suitable methods, such as reverse proteolysis (Fisch et al., *Bioconjugate Chem.*, 3:147-153 (1992); Werlen et al., *Bioconjugate Chem.*, 5:411-417 (1994); Kumaran et al., *Protein Sci.* 6(10):2233-2241 (1997); Itoh et al., *Bioorg. Chem.*, 24(1): 59-68 (1996); Capellas et al., *Biotechnol. Bioeng.*, 56(4):456-463 (1997)), and the methods described in Hermanson, G. T., *Bioconjugate Techniques*, Academic Press: San Diego, Calif. (1996).

Protein Scaffold Compositions Comprising Further Therapeutically Active Ingredients The protein scaffold compositions of the invention can optionally further comprise an effective amount of at least one compound or protein (small or large molecule) selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see, e.g., Nursing 2001 Handbook of Drugs, 21$^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

The anti-infective drug can be at least one selected from amebicides or at least one of antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, and miscellaneous anti-infectives. The CV drug can be at least one selected from inotropics, antiarrhythmics, antianginals, antihypertensives, antilipemics, and miscellaneous cardiovascular drugs. The CNS drug can be at least one selected from normarcotic analgesics or at least one selected from antipyretics, nonsteroidal anti-inflammatory drugs, narcotic or at least one opiod analgesics, sedative-hypnotics, anticonvulsants, antidepressants, antianxiety drugs, antipsychotics, central nervous system stimulants, antiparkinsonians, and miscellaneous central nervous system drugs. The ANS drug can be at least one selected from cholinergics (parasympathomimetics), anticholinergics, adrenergics (sympathomimetics), adrenergic blockers (sympatholytics), skeletal muscle relaxants, and neuromuscular blockers. The respiratory tract drug can be at least one selected from antihistamines, bronchodilators, expectorants or at least one antitussive, and miscellaneous respiratory drugs. The GI tract drug can be at least one selected from antacids or at least one adsorbent or at least one antiflatulent, digestive enzyme or at least one gallstone solubilizer, antidiarrheals, laxatives, antiemetics, and antiulcer drugs. The hormonal drug can be at least one selected from corticosteroids, androgens or at least one anabolic steroid, estrogen or at least one progestin, gonadotropin, antidiabetic drug or at least one glucagon, thyroid hormone, thyroid hormone antagonist, pituitary hormone, and parathyroid-like drug. The drug for fluid and electrolyte balance can be at least one selected from diuretics, electrolytes or at least one replacement solution, acidifier or at least one alkalinizer. The hematologic drug can be at least one selected from hematinics, anticoagulants, blood derivatives, and thrombolytic enzymes. The antineoplastics can be at least one selected from alkylating drugs, antimetabolites, antibiotic antineoplastics, antineoplastics that alter hormone balance, and miscellaneous antineoplastics. The immunomodulation drug can be at least one selected from immunosuppressants, vaccines or at least one toxoid, antitoxin or at least one antivenin, immune serum, and biological response modifier. The ophthalmic, otic, and nasal drugs can be at least one selected from ophthalmic anti-infectives, ophthalmic anti-inflammatories, miotics, mydriatics, ophthalmic vasoconstrictors, miscellaneous ophthalmics, otics, and nasal drugs. The topical drug can be at least one selected from local anti-infectives, scabicides or at least one pediculicide or topical corticosteroid. The nutritional drug can be at least one selected from vitamins, minerals, or calorics. See, e.g., contents of *Nursing* 2001 *Drug Handbook*, supra.

The at least one amebicide or antiprotozoal can be at least one selected from atovaquone, chloroquine hydrochloride, chloroquine phosphate, metronidazole, metronidazole hydrochloride, and pentamidine isethionate. The at least one anthelmintic can be at least one selected from mebendazole, pyrantel pamoate, and thiabendazole. The at least one antifungal can be at least one selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin, and terbinafine hydrochloride. The at least one antimalarial can be at least one selected from chloroquine hydrochloride, chloroquine phosphate, doxycycline, hydroxychloroquine sulfate, mefloquine hydrochloride, primaquine phosphate, pyrimethamine, and pyrimethamine with sulfadoxine. The at least one antituberculotic or antileprotic can be at least one selected from clofazimine, cycloserine, dapsone, ethambutol hydrochloride, isoniazid, pyrazinamide, rifabutin, rifampin, rifapentine, and streptomycin sulfate. The at least one aminoglycoside can be at least one selected from amikacin sulfate, gentamicin sulfate, neomycin sulfate, streptomycin sulfate, and tobramycin sulfate. The at least one penicillin can be at least one selected from amoxcillin/clavulanate potassium, amoxicillin trihydrate, ampicillin, ampicillin sodium, ampicillin trihydrate, ampicillin sodium/sulbactam sodium, cloxacillin sodium, dicloxacillin sodium, mezlocillin sodium, nafcillin sodium, oxacillin sodium, penicillin G benzathine, penicillin G potassium, penicillin G procaine, penicillin G sodium, penicillin V potassium, piperacillin sodium, piperacillin sodium/tazobactam sodium, ticarcillin disodium, and ticarcillin disodium/clavulanate potassium. The at least one cephalosporin can be at least one selected from cefaclor, cefadroxil, cefazolin sodium, cefdinir, cefepime hydrochloride, cefixime, cefmetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, and loracarbef. The at least one tetracycline can be at least one selected from demeclocycline hydrochloride, doxycycline calcium, doxycycline hyclate, doxycycline hydrochloride, doxycycline monohydrate, minocycline hydrochloride, and tetracycline hydrochloride. The at least one sulfonamide can be at least one selected from co-trimoxazole, sulfadiazine, sulfamethoxazole, sulfisoxazole, and sulfisoxazole acetyl. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, and trovafloxacin mesylate. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, and trovafloxacin mesylate. The at least one antiviral can be at least one selected from abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir, and zidovudine. The at least one macroline anti-infective can be at least one selected from azithromycin, clarithromycin, dirithromycin, erythromycin base, erythromycin estolate, erythromycin ethylsuccinate, erythromycin lactobionate, and erythromycin stearate. The at least one miscellaneous anti-infective can be at least one selected from aztreonam, bacitracin, chloramphenicol sodium sucinate, clindamycin hydrochloride, clindamycin palmitate hydrochloride, clindamycin phosphate, imipenem and cilastatin sodium, meropenem, nitrofurantoin macrocrystals, nitrofurantoin microcrystals, quinupristin/dalfopristin, spectinomycin hydrochloride, trimethoprim, and vancomycin hydrochloride. (See, e.g., pp. 24-214 of *Nursing* 2001 *Drug Handbook*.)

The at least one inotropic can be at least one selected from amrinone lactate, digoxin, and milrinone lactate. The at least one antiarrhythmic can be at least one selected from adenosine, amiodarone hydrochloride, atropine sulfate, bretylium tosylate, diltiazem hydrochloride, disopyramide, disopyramide phosphate, esmolol hydrochloride, flecamide acetate, ibutilide fumarate, lidocaine hydrochloride, mexiletine hydrochloride, moricizine hydrochloride, phenyloin, phenyloin sodium, procainamide hydrochloride, propafenone hydrochloride, propranolol hydrochloride, quinidine bisulfate, quinidine gluconate, quinidine polygalacturonate, quinidine sulfate, sotalol, tocainide hydrochloride, and verapamil hydrochloride. The at least one antianginal can be at least one selected from amlodipidine besylate, amyl nitrite, bepridil hydrochloride, diltiazem hydrochloride, isosorbide dinitrate, isosorbide mononitrate, nadolol, nicardipine hydrochloride, nifedipine, nitroglycerin, propranolol hydrochloride, verapamil, and verapamil hydrochloride. The at least one antihypertensive can be at least one selected from acebutolol hydrochloride, amlodipine besylate, atenolol, benazepril hydrochloride, betaxolol hydrochloride, bisoprolol fumarate, candesartan cilexetil, captopril, carteolol hydrochloride, carvedilol, clonidine, clonidine hydrochloride, diazoxide, diltiazem hydrochloride, doxazosin mesylate, enalaprilat, enalapril maleate, eprosartan mesylate, felodipine, fenoldopam mesylate, fosinopril sodium, guanabenz acetate, guanadrel sulfate, guanfacine hydrochloride, hydralazine hydrochloride, irbesartan, isradipine, labetalol hydrchloride, lisinopril, losartan potassium, methyldopa, methyldopate hydrochloride, metoprolol succinate, metoprolol tartrate, minoxidil, moexipril hydrochloride, nadolol, nicardipine hydrochloride, nifedipine, nisoldipine, nitroprusside sodium, penbutolol sulfate, perindopril erbumine, phentolamine mesylate, pindolol, prazosin hydrochloride, propranolol hydrochloride, quinapril hydrochloride, ramipril, telmisartan, terazosin hydrochloride, timolol maleate, trandolapril, valsartan, and verapamil hydrochloride. The at least one antilipemic can be at least one selected from atorvastatin calcium, cerivastatin sodium, cholestyramine, colestipol hydrochloride, fenofibrate (micronized), fluvastatin sodium, gemfibrozil, lovastatin, niacin, pravastatin sodium, and simvastatin. The at least one miscellaneous CV drug can be at least one selected from abciximab, alprostadil, arbutamine hydrochloride, cilostazol, clopidogrel bisulfate, dipyridamole, eptifibatide, midodrine hydrochloride, pentoxifylline, ticlopidine hydrochloride, and tirofiban hydrochloride. (See, e.g., pp. 215-336 of *Nursing* 2001 *Drug Handbook*.)

The at least one normarcotic analgesic or antipyretic can be at least one selected from acetaminophen, aspirin, choline magnesium trisalicylate, diflunisal, and magnesium salicylate. The at least one nonsteroidal anti-inflammatory drug can be at least one selected from celecoxib, diclofenac potassium, diclofenac sodium, etodolac, fenoprofen calcium, flurbiprofen, ibuprofen, indomethacin, indomethacin sodium trihydrate, ketoprofen, ketorolac tromethamine, nabumetone, naproxen, naproxen sodium, oxaprozin, piroxicam, rofecoxib, and sulindac. The at least one narcotic or opiod analgesic can be at least one selected from alfentanil hydrochloride, buprenorphine hydrochloride, butorphanol tartrate, codeine phosphate, codeine sulfate, fentanyl citrate, fentanyl transdermal system, fentanyl transmucosal, hydromorphone hydrochloride, meperidine hydrochloride, methadone hydrochloride, morphine hydrochloride, morphine sulfate, morphine tartrate, nalbuphine hydrochloride, oxycodone hydrochloride, oxycodone pectinate, oxymorphone hydrochloride, pentazocine hydrochloride, pentazocine hydrochloride and naloxone hydrochloride, pentazocine lactate, propoxyphene hydrochloride, propoxyphene napsylate, remifentanil hydrochloride, sufentanil citrate, and tramadol hydrochloride. The at least one sedative-hypnotic can be at least one selected from chloral hydrate, estazolam, flurazepam hydrochloride, pentobarbital, pentobarbital sodium, phenobarbital sodium, secobarbital sodium, temazepam, triazolam, zaleplon, and zolpidem tartrate. The at least one anticonvulsant can be at least one selected from acetazolamide sodium, carbamazepine, clonazepam, clorazepate dipotassium, diazepam, divalproex sodium, ethosuximde, fosphenytoin sodium, gabapentin, lamotrigine, magnesium sulfate, phenobarbital, phenobarbital sodium, phenyloin, phenyloin sodium, phenyloin sodium (extended), primidone, tiagabine hydrochloride, topiramate, valproate sodium, and valproic acid. The at least one antidepressant can be at least one selected from amitriptyline hydrochloride, amitriptyline pamoate, amoxapine, bupropion hydrochloride, citalopram hydrobromide, clomipramine hydrochloride, desipramine hydrochloride, doxepin hydrochloride, fluoxetine hydrochloride, imipramine hydrochloride, imipramine pamoate, mirtazapine, nefazodone hydrochloride, nortriptyline hydrochloride, paroxetine hydrochloride, phenelzine sulfate, sertraline hydrochloride, tranylcypromine sulfate, trimipramine maleate, and venlafaxine hydrochloride. The at least one antianxiety drug can be at least one selected from alprazolam, buspirone hydrochloride, chlordiazepoxide, chlordiazepoxide hydrochloride, clorazepate dipotassium, diazepam, doxepin hydrochloride, hydroxyzine embonate, hydroxyzine hydrochloride, hydroxyzine pamoate, lorazepam, mephrobamate, midazolam hydrochloride, and oxazepam. The at least one antipsychotic drug can be at least one selected from chlorpromazine hydrochloride, clozapine, fluphenazine decanoate, fluephenazine enanthate, fluphenazine hydrochloride, haloperidol, haloperidol decanoate, haloperidol lactate, loxapine hydrochloride, loxapine succinate, mesoridazine besylate, molindone hydrochloride, olanzapine, perphenazine, pimozide, prochlorperazine, quetiapine fumarate, risperidone, thioridazine hydrochloride, thiothixene, thiothixene hydrochloride, and trifluoperazine hydrochloride. The at least one central nervous system stimulant can be at least one selected from amphetamine sulfate, caffeine, dextroamphetamine sulfate, doxapram hydrochloride, methamphetamine hydrochloride, methylphenidate hydrochloride, modafinil, pemoline, and phentermine hydrochloride. The at least one antiparkinsonian can be at least one selected from amantadine hydrochloride, benztropine mesylate, biperiden hydrochloride, biperiden lactate, bromocriptine mesylate, carbidopa-levodopa, entacapone, levodopa, pergolide mesylate, pramipexole dihydrochloride, ropinirole hydrochloride, selegiline hydrochloride, tolcapone, and trihexyphenidyl hydrochloride. The at least one miscellaneous central nervous system drug can be at least one selected from bupropion hydrochloride, donepezil hydrochloride, droperidol, fluvoxamine maleate, lithium carbonate, lithium citrate, naratriptan hydrochloride, nicotine polacrilex, nicotine transdermal system, propofol, rizatriptan benzoate, sibutramine hydrochloride monohydrate, sumatriptan succinate, tacrine hydrochloride, and zolmitriptan. (See, e.g., pp. 337-530 of *Nursing* 2001 *Drug Handbook*.)

The at least one cholinergic (e.g., parasymathomimetic) can be at least one selected from bethanechol chloride, edrophonium chloride, neostigmine bromide, neostigmine methylsulfate, physostigmine salicylate, and pyridostigmine bromide. The at least one anticholinergic can be at least one selected from atropine sulfate, dicyclomine hydrochloride, glycopyrrolate, hyoscyamine, hyoscyamine sulfate, propantheline bromide, scopolamine, scopolamine butylbromide, and scopolamine hydrobromide. The at least one adrenergic (sympathomimetics) can be at least one selected from dobutamine hydrochloride, dopamine hydrochloride, metaraminol bitartrate, norepinephrine bitartrate, phenylephrine hydrochloride, pseudoephedrine hydrochloride, and pseudoephedrine sulfate. The at least one adrenergic blocker (sympatholytic) can be at least one selected from dihydroergotamine mesylate, ergotamine tartrate, methysergide maleate, and propranolol hydrochloride. The at least one skeletal muscle relaxant can be at least one selected from baclofen, carisoprodol, chlorzoxazone, cyclobenzaprine hydrochloride, dantrolene sodium, methocarbamol, and tizanidine hydrochloride. The at least one neuromuscular blocker can be at least one selected from atracurium besylate, cisatracurium besylate, doxacurium chloride, mivacurium chloride, pancuronium bromide, pipecuronium bromide, rapacuronium bromide, rocuronium bromide, succinylcholine chloride, tubocurarine chloride, and vecuronium bromide. (See, e.g., pp. 531-84 of *Nursing* 2001 *Drug Handbook*.)

The at least one antihistamine can be at least one selected from brompheniramine maleate, cetirizine hydrochloride, chlorpheniramine maleate, clemastine fumarate, cyproheptadine hydrochloride, diphenhydramine hydrochloride, fexofenadine hydrochloride, loratadine, promethazine hydrochloride, promethazine theoclate, and triprolidine hydrochloride. The at least one bronchodilator can be at least one selected from albuterol, albuterol sulfate, aminophylline, atropine sulfate, ephedrine sulfate, epinephrine, epinephrine bitartrate, epinephrine hydrochloride, ipratropium bromide, isoproterenol, isoproterenol hydrochloride, isoproterenol sulfate, levalbuterol hydrochloride, metaproterenol sulfate, oxtriphylline, pirbuterol acetate, salmeterol xinafoate, terbutaline sulfate, and theophylline. The at least one expectorant or antitussive can be at least one selected from benzonatate, codeine phosphate, codeine sulfate, dextramethorphan hydrobromide, diphenhydramine hydrochloride, guaifenesin, and hydromorphone hydrochloride. The at least one miscellaneous respiratory drug can be at least one selected from acetylcysteine, beclomethasone dipropionate, beractant, budesonide, calfactant, cromolyn sodium, dornase alfa, epoprostenol sodium, flunisolide, fluticasone propionate, montelukast sodium, nedocromil sodium, palivizumab, triamcinolone acetonide, zafirlukast, and zileuton. (See, e.g., pp. 585-642 of *Nursing* 2001 *Drug Handbook*.)

The at least one antacid, adsorbent, or antiflatulent can be at least one selected from aluminum carbonate, aluminum hydroxide, calcium carbonate, magaldrate, magnesium hydroxide, magnesium oxide, simethicone, and sodium bicarbonate. The at least one digestive enzyme or gallstone solubilizer can be at least one selected from pancreatin, pancrelipase, and ursodiol. The at least one antidiarrheal can be at least one selected from attapulgite, bismuth subsalicylate, calcium polycarbophil, diphenoxylate hydrochloride and atropine sulfate, loperamide, octreotide acetate, opium tincture, and opium tincure (camphorated). The at least one laxative can be at least one selected from bisocodyl, calcium polycarbophil, cascara sagrada, cascara sagrada aromatic fluidextract, cascara sagrada fluidextract, castor oil, docusate calcium, docusate sodium, glycerin, lactulose, magnesium citrate, magnesium hydroxide, magnesium sulfate, methylcellulose, mineral oil, polyethylene glycol or electrolyte solution, psyllium, senna, and sodium phosphates. The at least one antiemetic can be at least one selected from chlorpromazine hydrochloride, dimenhydrinate, dolasetron mesylate, dronabinol, granisetron hydrochloride, meclizine hydrochloride, metocloproamide hydrochloride, ondansetron hydrochloride, perphenazine, prochlorperazine, prochlorperazine edisylate, prochlorperazine maleate, promethazine hydrochloride, scopolamine, thiethylperazine maleate, and trimethobenzamide hydrochloride. The at least one antiulcer drug can be at least one selected from cimetidine, cimetidine hydrochloride, famotidine, lansoprazole, misoprostol, nizatidine, omeprazole, rabeprozole sodium, rantidine bismuth citrate, ranitidine hydrochloride, and sucralfate. (See, e.g., pp. 643-95 of *Nursing* 2001 *Drug Handbook*.)

The at least one corticosteroid can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, and triamcinolone diacetate. The at least one androgen or anabolic steroid can be at least one selected from danazol, fluoxymesterone, methyltestosterone, nandrolone decanoate, nandrolone phenpropionate, testosterone, testosterone cypionate, testosterone enanthate, testosterone propionate, and testosterone transdermal system. The at least one estrogen or progestin can be at least one selected from esterified estrogens, estradiol, estradiol cypionate, estradiol/norethindrone acetate transdermal system, estradiol valerate, estrogens (conjugated), estropipate, ethinyl estradiol, ethinyl estradiol and desogestrel, ethinyl estradiol and ethynodiol diacetate, ethinyl estradiol and desogestrel, ethinyl estradiol and ethynodiol diacetate, ethinyl estradiol and levonorgestrel, ethinyl estradiol and norethindrone, ethinyl estradiol and norethindrone acetate, ethinyl estradiol and norgestimate, ethinyl estradiol and norgestrel, ethinyl estradiol and norethindrone and acetate and ferrous fumarate, levonorgestrel, medroxyprogesterone acetate, mestranol and norethindron, norethindrone, norethindrone acetate, norgestrel, and progesterone. The at least one gonadroptropin can be at least one selected from ganirelix acetate, gonadoreline acetate, histrelin acetate, and menotropins. The at least one antidiabetic or glucaon can be at least one selected from acarbose, chlorpropamide, glimepiride, glipizide, glucagon, glyburide, insulins, metformin hydrochloride, miglitol, pioglitazone hydrochloride, repaglinide, rosiglitazone maleate, and troglitazone. The at least one thyroid hormone can be at least one selected from levothyroxine sodium, liothyronine sodium, liotrix, and thyroid. The at least one thyroid hormone antagonist can be at least one selected from methimazole, potassium iodide, potassium iodide (saturated solution), propylthiouracil, radioactive iodine (sodium iodide $^{131}$I), and strong iodine solution. The at least one pituitary hormone can be at least one selected from corticotropin, cosyntropin, desmophressin acetate, leuprolide acetate, repository corticotropin, somatrem, somatropin, and vasopressin. The at least one parathyroid-like drug can be at least one selected from calcifediol, calcitonin (human), calcitonin (salmon), calcitriol, dihydrotachysterol, and etidronate disodium. (See, e.g., pp. 696-796 of Nursing 2001 Drug Handbook.)

The at least one diuretic can be at least one selected from acetazolamide, acetazolamide sodium, amiloride hydrochloride, bumetanide, chlorthalidone, ethacrynate sodium, ethacrynic acid, furosemide, hydrochlorothiazide, indapamide, mannitol, metolazone, spironolactone, torsemide, triamterene, and urea. The at least one electrolyte or replacement solution can be at least one selected from calcium acetate, calcium carbonate, calcium chloride, calcium citrate, calcium glubionate, calcium gluceptate, calcium gluconate, calcium lactate, calcium phosphate (dibasic), calcium phosphate (tribasic), dextran (high-molecular-weight), dextran (low-molecular-weight), hetastarch, magnesium chloride, magnesium sulfate, potassium acetate, potassium bicarbonate, potassium chloride, potassium gluconate, Ringer's injection, Ringer's injection (lactated), and sodium chloride. The at least one acidifier or alkalinizer can be at least one selected from sodium bicarbonate, sodium lactate, and tromethamine. (See, e.g., pp. 797-833 of Nursing 2001 Drug Handbook.)

The at least one hematinic can be at least one selected from ferrous fumarate, ferrous gluconate, ferrous sulfate, ferrous sulfate (dried), iron dextran, iron sorbitol, polysaccharide-iron complex, and sodium ferric gluconate complex. The at least one anticoagulant can be at least one selected from ardeparin sodium, dalteparin sodium, danaparoid sodium, enoxaparin sodium, heparin calcium, heparin sodium, and warfarin sodium. The at least one blood derivative can be at least one selected from albumin 5%, albumin 25%, antihemophilic factor, anti-inhibitor coagulant complex, antithrombin III (human), factor IX (human), factor IX complex, and plasma protein fractions. The at least one thrombolytic enzyme can be at least one selected from alteplase, anistreplase, reteplase (recombinant), streptokinase, and urokinase. (See, e.g., pp. 834-66 of Nursing 2001 Drug Handbook.)

The at least one alkylating drug can be at least one selected from busulfan, carboplatin, carmustine, chlorambucil, cisplatin, cyclophosphamide, ifosfamide, lomustine, mechlorethamine hydrochloride, melphalan, melphalan hydrochloride, streptozocin, temozolomide, and thiotepa. The at least one antimetabolite can be at least one selected from capecitabine, cladribine, cytarabine, floxuridine, fludarabine phosphate, fluorouracil, hydroxyurea, mercaptopurine, methotrexate, methotrexate sodium, and thioguanine. The at least one antibiotic antineoplastic can be at least one selected from bleomycin sulfate, dactinomycin, daunorubicin citrate liposomal, daunorubicin hydrochloride, doxorubicin hydrochloride, doxorubicin hydrochloride liposomal, epirubicin hydrochloride, idarubicin hydrochloride, mitomycin, pentostatin, plicamycin, and valrubicin. The at least one antineoplastic that alters hormone balance can be at least one selected from anastrozole, bicalutamide, estramustine phosphate sodium, exemestane, flutamide, goserelin acetate, letrozole, leuprolide acetate, megestrol acetate, nilutamide, tamoxifen citrate, testolactone, and toremifene citrate. The at least one miscellaneous antineoplastic can be at least one selected from asparaginase, bacillus Calmette-Guerin (BCG) (live intravesical), dacarbazine, docetaxel, etoposide, etoposide phosphate, gemcitabine hydrochloride, irinotecan hydrochloride, mitotane, mitoxantrone hydrochloride, paclitaxel, pegaspargase, porfimer sodium, procarbazine hydrochloride, rituximab, teniposide, topotecan hydrochloride, trastuzumab, tretinoin, vinblastine sulfate, vincristine sulfate, and vinorelbine tartrate. (See, e.g., pp. 867-963 of Nursing 2001 Drug Handbook.)

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, and tacrolimus. The at least one vaccine or toxoid can be at least one selected from BCG vaccine, cholera vaccine, diphtheria and tetanus toxoids (adsorbed), diphtheria and tetanus toxoids and acellular pertussis vaccine adsorbed, diphtheria and tetanus toxoids and whole-cell pertussis vaccine, Haemophilus b conjugate vaccines, hepatitis A vaccine (inactivated), hepatisis B vaccine (recombinant), influenza virus vaccine 1999-2000 trivalent types A & B (purified surface antigen), influenza virus vaccine 1999-2000 trivalent types A & B (subvirion or purified subvirion), influenza virus vaccine 1999-2000 trivalent types A & B (whole virion), Japanese encephalitis virus vaccine (inactivated), Lyme disease vaccine (recombinant OspA), measles and mumps and rubella virus vaccine (live), measles and mumps and rubella virus vaccine (live attenuated), measles virus vaccine (live attenuated), meningococcal polysaccharide vaccine, mumps virus vaccine (live), plague vaccine, pneumococcal vaccine (polyvalent), poliovirus vaccine (inactivated), poliovirus vaccine (live, oral, trivalent), rabies vaccine (adsorbed), rabies vaccine (human diploid cell), rubella and mumps virus vaccine (live), rubella virus vaccine (live, attenuated), tetanus toxoid (adsorbed), tetanus toxoid (fluid), typhoid vaccine (oral), typhoid vaccine (parenteral), typhoid Vi polysaccharide vaccine, varicella virus vaccine, and yellow fever vaccine. The at least one antitoxin or antivenin can be at least one selected from black widow spider antivenin, Crotalidae antivenom (polyvalent), diphtheria antitoxin (equine), amd Micrurus fulvius antivenin. The at least one immune serum can be at least one selected from cytomegalovirus immune globulin (intraveneous), hepatitis B immune globulin (human), immune globulin intramuscular, immune globulin intravenous, rabies immune globulin (human), respiratory syncytial virus immune globulin intravenous (human), $Rh_0(D)$ immune globulin (human), $Rh_0(D)$ immune globulin intravenous (human), tetanus immune globulin (human), and varicella-zoster immune globulin. The at least one biological response modifier can be at least one selected from aldesleukin, epoetin alfa, filgrastim, glatiramer acetate for injection, interferon alfacon-1, interferon alfa-2a (recombinant), interferon alfa-2b (recombinant), interferon beta-1a, interferon beta-1b (recombinant), interferon gamma-1b, levamisole hydrochloride, oprelvekin, and sargramostim. (See, e.g., pp. 964-1040 of Nursing 2001 Drug Handbook.)

The at least one ophthalmic anti-infective can be selected form bacitracin, chloramphenicol, ciprofloxacin hydrochloride, erythromycin, gentamicin sulfate, ofloxacin 0.3%, polymyxin B sulfate, sulfacetamide sodium 10%, sulfacetamide sodium 15%, sulfacetamide sodium 30%, tobramycin, and vidarabine. The at least one ophthalmic anti-inflammatory can be at least one selected from dexamethasone, dexamethasone sodium phosphate, diclofenac sodium 0.1%, fluorometholone, flurbiprofen sodium, ketorolac tromethamine, prednisolone acetate (suspension) and prednisolone sodium phosphate (solution). The at least one miotic can be at least one selected from acetylocholine chloride, carbachol (intraocular), carbachol (topical), echothiophate iodide, pilocarpine, pilocarpine hydrochloride, and pilocarpine nitrate. The at least one mydriatic can be at least one selected from atropine sulfate, cyclopentolate hydrochloride, epinephrine hydrochloride, epinephryl borate, homatropine hydrobromide, phenylephrine hydrochloride, scopolamine hydrobromide, and tropicamide. The at least one ophthalmic vasoconstrictor can be at least one selected from naphazoline hydrochloride, oxymetazoline hydrochloride, and tetrahydrozoline hydrochloride. The at least one miscellaneous ophthalmic can be at least one selected from apraclonidine hydrochloride, betaxolol hydrochloride, brimonidine tartrate, carteolol hydrochloride, dipivefrin hydrochloride, dorzolamide hydrochloride, emedastine difumarate, fluorescein sodium, ketotifen fumarate, latanoprost, levobunolol hydrochloride, metipranolol hydrochloride, sodium chloride (hypertonic), and timolol maleate. The at least one otic can be at least one selected from boric acid, carbamide peroxide, chloramphenicol, and triethanolamine polypeptide oleate-condensate. The at least one nasal drug can be at least one selected from beclomethasone dipropionate, budesonide, ephedrine sulfate, epinephrine hydrochloride, flunisolide, fluticasone propionate, naphazoline hydrochloride, oxymetazoline hydrochloride, phenylephrine hydrochloride, tetrahydrozoline hydrochloride, triamcinolone acetonide, and xylometazoline hydrochloride. (See, e.g., pp. 1041-97 of *Nursing* 2001 *Drug Handbook*.)

The at least one local anti-infective can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, and tolnaftate. The at least one scabicide or pediculicide can be at least one selected from crotamiton, lindane, permethrin, and pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocorisone valerate, mometasone furoate, and triamcinolone acetonide. (See, e.g., pp. 1098-1136 of *Nursing* 2001 *Drug Handbook*.)

The at least one vitamin or mineral can be at least one selected from vitamin A, vitamin B complex, cyanocobalamin, folic acid, hydroxocobalamin, leucovorin calcium, niacin, niacinamide, pyridoxine hydrochloride, riboflavin, thiamine hydrochloride, vitamin C, vitamin D, cholecalciferol, ergocalciferol, vitamin D analogue, doxercalciferol, paricalcitol, vitamin E, vitamin K analogue, phytonadione, sodium fluoride, sodium fluoride (topical), trace elements, chromium, copper, iodine, manganese, selenium, and zinc. The at least one caloric can be at least one selected from amino acid infusions (crystalline), amino acid infusions in dextrose, amino acid infusions with electrolytes, amino acid infusions with electrolytes in dextrose, amino acid infusions for hepatic failure, amino acid infusions for high metabolic stress, amino acid infusions for renal failure, dextrose, fat emulsions, and medium-chain triglycerides. (See, e.g., pp. 1137-63 of *Nursing* 2001 *Drug Handbook*.)

Protein scaffold compositions of the present invention can further comprise at least one of any suitable and effective amount of a composition or pharmaceutical composition comprising a protein scaffold contacted or administered to a cell, tissue, organ, animal or patient in need of such modulation, treatment or therapy, optionally further comprising at least one selected from at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, etanercept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Non-limiting examples of such cytokines include, but are not limited to, any of IL-1 to IL-28 (e.g., IL-1, IL-2, etc.). Suitable dosages are well known in the art. See, e.g., Wells et al., eds., Pharmacotherapy Handbook, 2$^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer or anti-infectives can also include toxin molecules that are associated, bound, co-formulated or co-administered with at least one protein scaffold of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella cytotoxin, Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii,* and *Shigella sonnei*), *Salmonella* species (e.g., *Salmonella typhi, Salmonella cholerasuis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophile, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa*, and *Streptococci*. See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, N.Y. (1990); Berkow et al, eds., *The Merck Manual*, 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

Protein scaffold compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences*, 18$^{th}$ Edition, Mack Publishing Co. (Easton, Pa.) 1990. Pharmaceutically acceptable carriers can be routinely selected that are suitable for the mode of administration, solubility and/or stability of the protein scaffold, fragment or variant composition as well known in the art or as described herein.

Pharmaceutical excipients and additives useful in the present composition include, but are not limited to, proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Exemplary protein excipients include serum albumin, such as human serum albumin (HSA), recombinant human albumin (rHA), gelatin, casein, and the like. Representative amino acid/protein components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Protein scaffold compositions can also include a buffer or a pH-adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts, such as citrate.

Additionally, protein scaffold compositions of the invention can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates, such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the protein scaffold, portion or variant compositions according to the invention are known in the art, e.g., as listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents. An exemplary carrier molecule is the mucopolysaccharide, hyaluronic acid, which may be useful for intraarticular delivery.

Formulations

As noted above, the invention provides for stable formulations, which preferably comprise a phosphate buffer with saline or a chosen salt, as well as preserved solutions and formulations containing a preservative as well as multi-use preserved formulations suitable for pharmaceutical or veterinary use, comprising at least one protein scaffold in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, polymers, or mixtures thereof in an aqueous diluent. Any suitable concentration or mixture can be used as known in the art, such as about 0.0015%, or any range, value, or fraction therein. Non-limiting examples include, no preservative, about 0.1-2% m-cresol (e.g., 0.2, 0.3. 0.4, 0.5, 0.9, 1.0%), about 0.1-3% benzyl alcohol (e.g., 0.5, 0.9, 1.1, 1.5, 1.9, 2.0, 2.5%), about 0.001-0.5% thimerosal (e.g., 0.005, 0.01), about 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one protein scaffold with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one protein scaffold, and a second vial comprising an aqueous diluent of prescribed buffer or preservative, wherein said packaging material comprises a label that instructs a patient to reconstitute the at least one protein scaffold in the aqueous diluent to form a solution that can be held over a period of twenty-four hours or greater.

The at least one protein scaffold used in accordance with the present invention can be produced by recombinant means, including from mammalian cell or transgenic preparations, or can be purified from other biological sources, as described herein or as known in the art.

The range of at least one protein scaffold in the product of the present invention includes amounts yielding upon reconstitution, if in a wet/dry system, concentrations from about 1.0 μg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g., isotonicity agents, buffers, antioxidants, and preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably, the formulations of the present invention have a pH between about 6.8 and about 7.8. Preferred buffers include phosphate buffers, most preferably, sodium phosphate, particularly, phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants, such as polysorbate 20 or 80 or poloxamer 184 or 188, Pluronic® polyls, other block co-polymers, and chelators, such as EDTA and EGTA, can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one protein scaffold and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one protein scaffold and preservative in an aqueous diluent is carried out using conventional dissolution and mixing procedures. To prepare a suitable formulation, for example, a measured amount of at least one protein scaffold in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized at least one protein scaffold that is reconstituted with a second vial containing water, a preservative and/or excipients, preferably, a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period ranging from immediate to twenty-four hours or greater. Accordingly, the presently claimed articles of manufacture offer significant advantages to the patient. Formulations of the invention can optionally be safely stored at temperatures of from about 2° C. to about 40° C. and retain the biological activity of the protein for extended periods of time, thus allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of at least one protein scaffold of the invention can be prepared by a process that comprises mixing at least one protein scaffold in an aqueous diluent. Mixing is carried out using conventional dissolution and mixing procedures. To prepare a suitable diluent, for example, a measured amount of at least one protein scaffold in water or buffer is combined in quantities sufficient to provide the protein and, optionally, a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one protein scaffold that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one protein scaffold that is reconstituted with a second vial containing the aqueous diluent. The clear solution in this case can be up to one liter or even larger in size, providing a large reservoir from which smaller portions of the at least one protein scaffold solution can be retrieved one or multiple times for transfer into smaller vials and provided by the pharmacy or clinic to their customers and/or patients.

Recognized devices comprising single vial systems include pen-injector devices for delivery of a solution, such as BD Pens, BD Autojector®, Humaject®, NovoPen®, B-D®Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, e.g., as made or developed by Becton Dickensen (Franklin Lakes, N.J., www.bectondickenson.com), Disetronic (Burgdorf, Switzerland, www.disetronic.com; Bioject, Portland, Oreg. (www.bioject.com); National Medical Products, Weston Medical (Peterborough, UK, www.weston-medical.com), Medi-Ject Corp (Minneapolis, Minn., www.mediject.com), and similarly suitable devices. Recognized devices comprising a dual vial system include those pen-injector systems for reconstituting a lyophilized drug in a cartridge for delivery of the reconstituted solution, such as the HumatroPen®. Examples of other devices suitable include pre-filled syringes, auto-injectors, needle free injectors and needle free IV infusion sets.

The products presently claimed include packaging material. The packaging material provides, in addition to the information required by the regulatory agencies, the conditions under which the product can be used. The packaging material of the present invention provides instructions to the patient to reconstitute at least one protein scaffold in the aqueous diluent to form a solution and to use the solution over a period of 2-24 hours or greater for the two vial, wet/dry, product. For the single vial, solution product, the label indicates that such solution can be used over a period of 2-24 hours or greater. The presently claimed products are useful for human pharmaceutical product use.

The formulations of the present invention can be prepared by a process that comprises mixing at least one protein scaffold and a selected buffer, preferably, a phosphate buffer containing saline or a chosen salt. Mixing at least one protein scaffold and buffer in an aqueous diluent is carried out using conventional dissolution and mixing procedures. To prepare a suitable formulation, for example, a measured amount of at least one protein scaffold in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized protein scaffold that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

Other formulations or methods of stabilizing the protein scaffold may result in other than a clear solution of lyophilized powder comprising the protein scaffold. Among non-clear solutions are formulations comprising particulate suspensions, said particulates being a composition containing the protein scaffold in a structure of variable dimension and known variously as a microsphere, microparticle, nanoparticle, nanosphere, or liposome. Such relatively homogenous, essentially spherical, particulate formulations containing an active agent can be formed by contacting an aqueous phase containing the active agent and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active agent and a polymer dispersed in a continuous solvent and removing said solvent from the suspension by freeze-drying or dilution-extraction-precipitation as taught in U.S. Pat. No. 4,818,542. Preferred polymers for such preparations are natural or synthetic copolymers or polymers selected from the group consisting of gleatin agar, starch, arabinogalactan, albumin, collagen, polyglycolic acid, polylactic aced, glycolide-L(−) lactide poly(episilon-caprolactone, poly(epsilon-caprolactone-CO-lactic acid), poly(epsilon-caprolactone-CO-glycolic acid), poly(β-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic aced, glycolide-L(−) lactide poly(episilon-caprolactone, poly (epsilon-caprolactone-CO-lactic acid), and poly(epsilon-caprolactone-CO-glycolic acid. Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase may include pressure forcing said first phase through an orifice in a nozzle to affect droplet formation.

Dry powder formulations may result from processes other than lyophilization, such as by spray drying or solvent extraction by evaporation or by precipitation of a crystalline composition followed by one or more steps to remove aqueous or nonaqueous solvent. Preparation of a spray-dried protein scaffold preparation is taught in U.S. Pat. No. 6,019,968. The protein scaffold-based dry powder compositions may be produced by spray drying solutions or slurries of the protein scaffold and, optionally, excipients, in a solvent under conditions to provide a respirable dry powder. Solvents may include polar compounds, such as water and ethanol, which may be readily dried. Protein scaffold stability may be enhanced by performing the spray drying procedures in the absence of oxygen, such as under a nitrogen blanket or by using nitrogen as the drying gas. Another relatively dry formulation is a dispersion of a plurality of perforated microstructures dispersed in a suspension medium that typically comprises a hydrofluoroalkane propellant as taught in WO 9916419. The stabilized dispersions may be administered to the lung of a patient using a metered dose inhaler. Equipment useful in the commercial manufacture of spray dried medicaments are manufactured by Buchi Ltd. or Niro Corp.

At least one protein scaffold in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

The present invention also provides a method for modulating or treating a disease, in a cell, tissue, organ, animal, or patient, as known in the art or as described herein, using at least one protein scaffold of the present invention, e.g., administering or contacting the cell, tissue, organ, animal, or patient with a therapeutic effective amount of protein scaffold. The present invention also provides a method for modulating or treating a disease, in a cell, tissue, organ, animal, or patient including, but not limited to, at least one of obesity, an immune related disease, a cardiovascular disease, an infectious disease, a malignant disease or a neurologic disease.

The present invention also provides a method for modulating or treating at least one immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, osteolysis, aseptic loosening of orthopedic implants, inflammatory bowel disease, ulcerative colitis, systemic lupus erythematosus, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitivity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynaud's disease, type B insulin-resistant diabetes, asthma, myasthenia gravis, antibody-meditated cytotoxicity, type III hypersensitivity reactions, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited to, asthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The present invention also provides a method for modulating or treating at least one cardiovascular disease in a cell, tissue, organ, animal, or patient, including, but not limited to, at least one of cardiac stun syndrome, myocardial infarction, congestive heart failure, stroke, ischemic stroke, hemorrhage, acute coronary syndrome, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occlusion of the abdominal aorta and its branches, peripheral vascular disorders, occlusive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like. Such a method can optionally comprise administering an effective amount of a composition or pharmaceutical composition comprising at least one protein scaffold to a cell, tissue, organ, animal or patient in need of such modulation, treatment or therapy.

The present invention also provides a method for modulating or treating at least infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (e.g., A, B or C, or the like), septic arthritis, peritonitis, pneumonia, epiglottitis, *e. coli* 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium intracellulare, pneumocystis carinii* pneumonia, pelvic inflammatory disease, orchitis/epidydimitis, *legionella*, lyme disease, influenza a, epstein-barr virus, viral-associated hemaphagocytic syndrome, viral encephalitis/aseptic meningitis, and the like.

The present invention also provides a method for modulating or treating at least one malignant disease in a cell, tissue, organ, animal or patient, including, but not limited to, at least one of: leukemia, acute leukemia, acute lymphoblastic leukemia (ALL), acute lymphocytic leukemia, B-cell, T-cell or FAB ALL, acute myeloid leukemia (AML), acute myelogenous leukemia, chromic myelocytic leukemia (CML), chronic lymphocytic leukemia (CLL), hairy cell leukemia, myelodyplastic syndrome (MDS), a lymphoma, Hodgkin's disease, a malignamt lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, bladder cancer, breast cancer, colorectal cancer, endometiral cancer, head cancer, neck cancer, hereditary nonpolyposis cancer, Hodgkin's lymphoma, liver cancer, lung cancer, non-small cell lung cancer, ovarian cancer, pancreatic cancer, prostate cancer, renal cell carcinoma, testicular cancer, adenocarcinomas, sarcomas, malignant melanoma, hemangioma, metastatic disease, cancer related bone resorption, cancer related bone pain, and the like.

The present invention also provides a method for modulating or treating at least one neurologic disease in a cell, tissue, organ, animal or patient, including, but not limited to, at least one of: neurodegenerative diseases, multiple sclerosis, migraine headache, AIDS dementia complex, demyelinating diseases, such as multiple sclerosis and acute transverse myelitis; extrapyramidal and cerebellar disorders, such as lesions of the corticospinal system; disorders of the basal ganglia; hyperkinetic movement disorders, such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi-system disorder); demyelinating core disorders, such as multiple sclerosis, acute transverse myelitis; and disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; Dementia pugilistica; neurotraumatic injury (e.g., spinal cord injury, brain injury, concussion, repetitive concussion); pain; inflammatory pain; autism; depression; stroke; cognitive disorders; epilepsy; and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, $16^{th}$ Edition, Merck & Company, Rahway, N.J. (1992).

The present invention also provides a method for modulating or treating at least one wound, trauma or tissue injury or related chronic condition, in a cell, tissue, organ, animal or patient, including, but not limited to, at least one of: bodily injury or a trauma associated with oral surgery including periodontal surgery, tooth extraction(s), endodontic treatment, insertion of tooth implants, application and use of tooth prosthesis; or wherein the wound is selected from the group consisting of aseptic wounds, contused wounds, incised wounds, lacerated wounds, non-penetrating wounds, open wounds, penetrating wounds, perforating wounds, puncture wounds, septic wounds, infarctions and subcutaneous wounds; or wherein the wound is selected from the group consisting of ischemic ulcers, pressure sores, fistulae, severe bites, thermal burns and donor site wounds; or wherein the wound is anaphthous wound, a traumatic wound or a herpes associated wound.

Wounds and/or ulcers are normally found protruding from the skin or on a mucosal surface or as a result of an infarction in an organ ("stroke"). A wound may be a result of a soft tissue defect or a lesion or of an underlying condition. In the present context, the term "skin" relates to the outermost surface of the body of an animal, including a human, and embraces intact or almost intact skin as well as an injured skin surface. The term "mucosa" relates to undamaged or damaged mucosa of an animal, such as a human, and may be the oral, buccal, aural, nasal, lung, eye, gastrointestinal, vaginal, or rectal mucosa.

In the present context the term "wound" denotes a bodily injury with disruption of the normal integrity of tissue structures. The term is also intended to encompass the terms "sore," "lesion," "necrosis," and "ulcer." Normally, the term "sore" is a popular term for almost any lesion of the skin or mucous membranes and the term "ulcer" is a local defect, or excavation, of the surface of an organ or tissue, which is produced by the sloughing of necrotic tissue. Lesion generally relates to any tissue defect. Necrosis is related to dead tissue resulting from infection, injury, inflammation or infarctions.

The term "wound" used in the present context denotes any wound (see below for a classification of wounds) and at any particular stage in the healing process, including the stage before any healing has initiated or even before a specific wound like a surgical incision is made (prophylactic treatment). Examples of wounds which can be prevented and/or treated in accordance with the present invention are, e.g., aseptic wounds, contused wounds, incised wounds, lacerated wounds, non-penetrating wounds (i.e., wounds in which there is no disruption of the skin but there is injury to underlying structures), open wounds, penetrating wounds, perforating wounds, puncture wounds, septic wounds, subcutaneous wounds, etc. Examples of sores are bed sores, canker sores, chrome sores, cold sores, pressure sores, etc. Examples of ulcers are, e.g., a peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous ulcer, symptomatic ulcer, trophic ulcer, tropical ulcer, and veneral ulcer, e.g., caused by gonorrhoea (including urethritis, endocervicitis and proctitis). Conditions related to wounds or sores which may be successfully treated according to the invention are burns, anthrax, tetanus, gas gangrene, scarlatina, erysipelas, sycosis barbae, folliculitis, impetigo contagiosa, or impetigo bullosa, etc. There is often a certain overlap between the use of the terms "wound" and "ulcer" and "wound" and "sore" and, furthermore, the terms are often used at random. Therefore, as mentioned above, in the present context the term "wound" encompasses the terms "ulcer," "lesion," "sore" and "infarction," and the terms are indiscriminately used unless otherwise indicated.

The kinds of wounds to be treated according to the invention include also (i) general wounds, such as, e.g., surgical, traumatic, infectious, ischemic, thermal, chemical and bullous wounds; (ii) wounds specific for the oral cavity, such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and (iii) wounds on the skin, such as, e.g., neoplasm, burns (e.g. chemical, thermal), lesions (bacterial, viral, autoimmunological), bites and surgical incisions. Another way of classifying wounds is as (i) small tissue loss due to surgical incisions, minor abrasions and minor bites, or as (ii) significant tissue loss. The latter group includes ischemic ulcers, pressure sores, fistulae, lacerations, severe bites, thermal burns and donor site wounds (in soft and hard tissues) and infarctions.

Other wounds that are of importance in connection with the present invention are wounds like ischemic ulcers, pressure sores, fistulae, severe bites, thermal burns and donor site wounds. Ischemic ulcers and pressure sores are wounds which normally only heal very slowly and especially in such cases, an improved and more rapid healing process is of course of great importance for the patient. Furthermore, the costs involved in the treatment of patients suffering from such wounds are markedly reduced when the healing is improved and takes place more rapidly.

Donor site wounds are wounds which, e.g., occur in connection with removal of hard tissue from one part of the body to another part of the body, e.g., in connection with transplantation. The wounds resulting from such operations are very painful and an improved healing is therefore most valuable. The term "skin" is used in a very broad sense embracing the epidermal layer of the skin and—in those cases where the skin surface is more or less injured—also the dermal layer of the skin. Apart from the stratum corneum, the epidermal layer of the skin is the outer (epithelial) layer and the deeper connective tissue layer of the skin is called the dermis.

Any method of the present invention can comprise administering an effective amount of a composition or pharmaceutical composition comprising at least one protein scaffold to a cell, tissue, organ, animal or patient in need of such modulation, treatment or therapy. Such a method can optionally further comprise co-administration or combination therapy for treating such diseases or disorders, wherein the administering of said at least one protein scaffold, specified portion or variant thereof, further comprises administering, before concurrently, and/or after, at least one selected from at least one TNF antagonist (e.g., but not limited to, a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, etanercept (Enbrel™), adalimulab (Humira™), CDP-571, CDP-870, afelimomab, lenercept, and the like), an antirheumatic (e.g., methotrexate, auranofin, aurothioglucose, azathioprine, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000); Nursing 2001 Handbook of Drugs, $21^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J. each of which references are entirely incorporated herein by reference.

Cytokines include any known cytokine See, e.g., CopewithCytokines.com. Cytokine antagonists include, but are not limited to, any protein scaffold, antibody, fragment or mimetic, any soluble receptor, fragment or mimetic, any small molecule antagonist, or any combination thereof.

Typically, treatment of pathologic conditions is effected by administering an effective amount or dosage of at least protein scaffold composition that total, on average, a range from at least about 0.01 to 500 milligrams of at least one protein scaffold per kilogram of patient per dose, and, preferably, from at least about 0.1 to 100 milligrams protein scaffold/kilogram of patient per single or multiple administration, depending upon the specific activity of the active agent contained in the composition. Alternatively, the effective serum concentration can comprise 0.1-5000 µg/ml serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include about 0.1-99 and/or 100-500 mg/kg/administration, or any range, value or fraction thereof, or to achieve a serum concentration of about 0.1-5000 µg/ml serum concentration per single or multiple administration, or any range, value or fraction thereof. A preferred dosage range for the protein scaffold of the present invention is from about 1 mg/kg, up to about 3, about 6 or about 12 mg/kg of body weight of the patient.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably, 0.1 to 10 milligrams per kilogram per administration or in sustained release form is effective to obtain desired results.

As a non-limiting example, treatment of humans or animals can be provided as a one-time or periodic dosage of at least one protein scaffold of the present invention about 0.1 to 100 mg/kg or any range, value or fraction thereof per day, on at least one of day 1-40, or, alternatively or additionally, at least one of week 1-52, or, alternatively or additionally, at least one of 1-20 years, or any combination thereof, using single, infusion or repeated doses.

Dosage forms (composition) suitable for internal administration generally contain from about 0.001 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the protein scaffold can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and about 1-10% human serum albumin. Liposomes and nonaqueous vehicles, such as fixed oils, can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration

Many known and developed modes can be used according to the present invention for administering pharmaceutically effective amounts of at least one protein scaffold according to the present invention. While pulmonary administration is used in the following description, other modes of administration can be used according to the present invention with suitable results. Protein scaffolds of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration

Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semisynthetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

Alternative Delivery

The invention further relates to the administration of at least one protein scaffold by parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal means. At least one protein scaffold composition can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways, such as electroporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

Pulmonary/Nasal Administration

For pulmonary administration, preferably, at least one protein scaffold composition is delivered in a particle size effective for reaching the lower airways of the lung or sinuses. According to the invention, at least one protein scaffold can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of protein scaffolds are also known in the art. All such devices can use formulations suitable for the administration for the dispensing of protein scaffold in an aerosol. Such aerosols can be comprised of either solutions (both aqueous and non aqueous) or solid particles.

Metered dose inhalers like the Ventolin metered dose inhaler, typically use a propellent gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention.

Preferably, a composition comprising at least one protein scaffold is delivered by a dry powder inhaler or a sprayer. There are several desirable features of an inhalation device for administering at least one protein scaffold of the present invention. For example, delivery by the inhalation device is advantageously reliable, reproducible, and accurate. The inhalation device can optionally deliver small dry particles, e.g., less than about 10 μm, preferably about 1-5 μm, for good respirability.

Administration of Protein Scaffold Compositions as a Spray

A spray including protein scaffold composition can be produced by forcing a suspension or solution of at least one protein scaffold through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one protein scaffold composition delivered by a sprayer have a particle size less than about 10 µm, preferably, in the range of about 1 µm to about 5 µm, and, most preferably, about 2 µm to about 3 µm.

Formulations of at least one protein scaffold composition suitable for use with a sprayer typically include protein scaffold composition in an aqueous solution at a concentration of about 0.1 mg to about 100 mg of at least one protein scaffold composition per ml of solution or mg/gm, or any range, value, or fraction therein. The formulation can include agents, such as an excipient, a buffer, an isotonicity agent, a preservative, a surfactant, and, preferably, zinc. The formulation can also include an excipient or agent for stabilization of the protein scaffold composition, such as a buffer, a reducing agent, a bulk protein, or a carbohydrate. Bulk proteins useful in formulating protein scaffold compositions include albumin, protamine, or the like. Typical carbohydrates useful in formulating protein scaffold compositions include sucrose, mannitol, lactose, trehalose, glucose, or the like. The protein scaffold composition formulation can also include a surfactant, which can reduce or prevent surface-induced aggregation of the protein scaffold composition caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein, such as protein scaffolds, or specified portions or variants, can also be included in the formulation.

Administration of Protein Scaffold Compositions by a Nebulizer

Protein scaffold compositions of the invention can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of protein scaffold composition through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of protein scaffold composition either directly or through a coupling fluid, creating an aerosol including the protein scaffold composition. Advantageously, particles of protein scaffold composition delivered by a nebulizer have a particle size less than about 10 µm, preferably, in the range of about 1 µm to about 5 µm, and, most preferably, about 2 µm to about 3 µm.

Formulations of at least one protein scaffold suitable for use with a nebulizer, either jet or ultrasonic, typically include a concentration of about 0.1 mg to about 100 mg of at least one protein scaffold per ml of solution. The formulation can include agents, such as an excipient, a buffer, an isotonicity agent, a preservative, a surfactant, and, preferably, zinc. The formulation can also include an excipient or agent for stabilization of the at least one protein scaffold composition, such as a buffer, a reducing agent, a bulk protein, or a carbohydrate. Bulk proteins useful in formulating at least one protein scaffold compositions include albumin, protamine, or the like. Typical carbohydrates useful in formulating at least one protein scaffold include sucrose, mannitol, lactose, trehalose, glucose, or the like. The at least one protein scaffold formulation can also include a surfactant, which can reduce or prevent surface-induced aggregation of the at least one protein scaffold caused by atomization of the solution in forming an aerosol. Various conventional surfactants can be employed, such as polyoxyethylene fatty acid esters and alcohols, and polyoxyethylene sorbital fatty acid esters. Amounts will generally range between about 0.001 and 4% by weight of the formulation. Especially preferred surfactants for purposes of this invention are polyoxyethylene sorbitan monooleate, polysorbate 80, polysorbate 20, or the like. Additional agents known in the art for formulation of a protein, such as protein scaffold, can also be included in the formulation.

Administration of Protein Scaffold Compositions by a Metered Dose Inhaler

In a metered dose inhaler (MDI), a propellant, at least one protein scaffold, and any excipients or other additives are contained in a canister as a mixture including a liquefied compressed gas. Actuation of the metering valve releases the mixture as an aerosol, preferably containing particles in the size range of less than about 10 µm, preferably, about 1 µm to about 5 µm, and, most preferably, about 2 µm to about 3 µm. The desired aerosol particle size can be obtained by employing a formulation of protein scaffold composition produced by various methods known to those of skill in the art, including jet-milling, spray drying, critical point condensation, or the like. Preferred metered dose inhalers include those manufactured by 3M or Glaxo and employing a hydrofluorocarbon propellant. Formulations of at least one protein scaffold for use with a metered-dose inhaler device will generally include a finely divided powder containing at least one protein scaffold as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluoroalkane-134a), HFA-227 (hydrofluoroalkane-227), or the like. Preferably, the propellant is a hydrofluorocarbon. The surfactant can be chosen to stabilize the at least one protein scaffold as a suspension in the propellant, to protect the active agent against chemical degradation, and the like. Suitable surfactants include sorbitan trioleate, soya lecithin, oleic acid, or the like. In some cases, solution aerosols are preferred using solvents, such as ethanol. Additional agents known in the art for formulation of a protein can also be included in the formulation. One of ordinary skill in the art will recognize that the methods of the current invention can be achieved by pulmonary administration of at least one protein scaffold composition via devices not described herein.

Oral Formulations and Administration

Formulations for oral administration rely on the co-administration of adjuvants (e.g., resorcinols and nonionic surfactants, such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Formulations for delivery of hydrophilic agents including proteins and protein scaffolds and a combination of at least two surfactants intended for oral, buccal, mucosal, nasal, pulmonary, vaginal transmembrane, or rectal administration are taught in U.S. Pat. No. 6,309,663. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant, such as magnesium stearate, paraben, preserving agent, such as sorbic acid, ascorbic acid, .alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. No. 5,879,681 and U.S. Pat. No. 5,871,753 and used to deliver biologically active agents orally are known in the art.

Mucosal Formulations and Administration

A formulation for orally administering a bioactive agent encapsulated in one or more biocompatible polymer or copolymer excipients, preferably, a biodegradable polymer or copolymer, affording microcapsules which due to the proper size of the resultant microcapsules results in the agent reaching and being taken up by the folliculi lymphatic aggregati, otherwise known as the "Peyer's patch," or "GALT" of the animal without loss of effectiveness due to the agent having passed through the gastrointestinal tract. Similar folliculi lymphatic aggregati can be found in the bronchei tubes (BALT) and the large intestine. The above-described tissues are referred to in general as mucosally associated lymphoreticular tissues (MALT). For absorption through mucosal surfaces, compositions and methods of administering at least one protein scaffold include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g., suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration, excipients include sugars, calcium stearate, magnesium stearate, pregelinatined starch, and the like (U.S. Pat. No. 5,849,695).

Transdermal Formulations and Administration

For transdermal administration, the at least one protein scaffold is encapsulated in a delivery device, such as a liposome or polymeric nanoparticles, microparticle, microcapsule, or microspheres (referred to collectively as microparticles unless otherwise stated). A number of suitable devices are known, including microparticles made of synthetic polymers, such as polyhydroxy acids, such as polylactic acid, polyglycolic acid and copolymers thereof, polyorthoesters, polyanhydrides, and polyphosphazenes, and natural polymers, such as collagen, polyamino acids, albumin and other proteins, alginate and other polysaccharides, and combinations thereof (U.S. Pat. No. 5,814,599).

Prolonged Administration and Formulations

It can be desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid, such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation, such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b), e.g., a zinc tannate salt. Additionally, the compounds of the present invention or, preferably, a relatively insoluble salt, such as those just described, can be formulated in a gel, for example, an aluminum monostearate gel with, e.g., sesame oil, suitable for injection. Particularly preferred salts are zinc salts, zinc tannate salts, pamoate salts, and the like. Another type of slow release depot formulation for injection would contain the compound or salt dispersed for encapsulation in a slow degrading, non-toxic, non-antigenic polymer, such as a polylactic acid/polyglycolic acid polymer for example as described in U.S. Pat. No. 3,773,919. The compounds or, preferably, relatively insoluble salts, such as those described above, can also be formulated in cholesterol matrix silastic pellets, particularly for use in animals. Additional slow release, depot or implant formulations, e.g., gas or liquid liposomes, are known in the literature (U.S. Pat. No. 5,770,222 and "Sustained and Controlled Release Drug Delivery Systems", J. R. Robinson ed., Marcel Dekker, Inc., N.Y., 1978).

Having generally described the invention, the same will be more readily understood by reference to the following examples, which are provided by way of illustration and are not intended as limiting.

EXAMPLES

Example 1

Tencon Design

The third FN3 domain from human Tenascin (SEQ ID NO: 3) can be used as an alternative scaffold capable of being engineered to bind to specific target molecules via surface exposed loops structurally analogous to antibody complementarity determining regions (CDR). The melting temperature of this domain is 54° C. in PBS in its native form. In order to produce a scaffold molecule with a similar structure and improved physical properties, such as an improved thermal stability, a consensus sequence was designed based on an alignment of 15 FN3 domains from human Tenascin (SEQ ID NOS: 1-15).

Analysis of the multiple sequence alignment in Table 1 shows that these 15 domains have sequence identities to each other ranging from 13 to 80%, with an average sequence identity among pairs of 29%. A consensus sequence (SEQ ID NO: 16) was designed by incorporating the most conserved (frequent) amino acid at each position from the alignment shown in Table 1. In pairwise alignments, the consensus sequence of the present invention (SEQ ID NO:16), designated as Tencon, is identical to the FN3 domains from Tenascin at 34-59% of positions with an average sequence identity of 43%.

Expression and Purification

The amino acid sequence of Tencon (SEQ ID NO: 16) was back translated, resulting in the DNA sequence shown in SEQ ID NO: 17. This sequence was assembled by overlapping PCR, subcloned into a modified pET 15 vector, transformed into BL21Star(DE3) *E. coli* (Invitrogen) and plated onto LB agar plates containing 75 µg/mL carbenicillin. A single colony was picked and grown overnight at 37° C. in 50 ml of TB media containing 2% glucose and 100 µg/mL carbenicillin. This culture was used to seed 500 mL of autoinduction media (Overnight Express Instant TB media, Novagen) in a 2.5 L Ultra Yield flask (Thomson Instrument Company). The growth and expression was done using a dual program (3 hours at 37° C., 300 rpm, followed by 16 hours at 30° C., 250 rpm) in an ATR Multitron shaking incubator.

The culture was harvested and centrifuged at 7000 rpm for 15 minutes in a JL8.1 rotor to pellet the cells. The cells were resuspended in 30 ml buffer containing 20 mM sodium phosphate, pH 7.5, 500 mM NaCl, 10% glycerol, 20 mM imidazole, 0.37 mg/mL lysozyme, 1× Complete Protease inhibitor (EDTA-free; Roche) and Benzonase (Sigma-Aldrich, 0.25 µl/ml final) and lysed with a Misonix XL2020 sonicator for 5 minutes on ice in pulse mode (5 seconds on, 30 seconds off). The insoluble material was removed by centrifugation at 17,000 rpm for 30 minutes in a JA-17 rotor.

The Tencon protein was purified from the soluble lysate in a 2-step chromatographic process. First, the protein was captured by immobilized metal affinity chromatography, adding 2 mL Ni-NTA agarose beads (Qiagen) to the lysate and placing it on a rocking platform for 1 hour at 4° C. The resin was then packed into a Poly-Prep column (Bio-Rad) and washed with 20 mM sodium phosphate, pH 7.5, 500 mM NaCl, 10% glycerol and 20 mM imidazole to remove the unbound material. The proteins were eluted from the resin with 20 mM sodium phosphate, pH 7.5, 500 mM NaCl, 10% glycerol and 500 mM imidazole. The fractions were analyzed by SDS-PAGE, both by Coomassie stain and by Western blot using an HRP-conjugated anti-His antibody (Immunology Consultants Laboratory). The desired fractions were pooled and dialyzed into PBS pH 7.4. As a second purification step the protein was loaded onto a Superdex-75 HiLoad 16/60 column (GE Healthcare) equilibrated in PBS. The fractions were analyzed by SDS-PAGE, and the fractions containing Tencon were pooled and concentrated using a Centriprep UltraCel YM-3 concentrator (Amicon).

Figure 1:
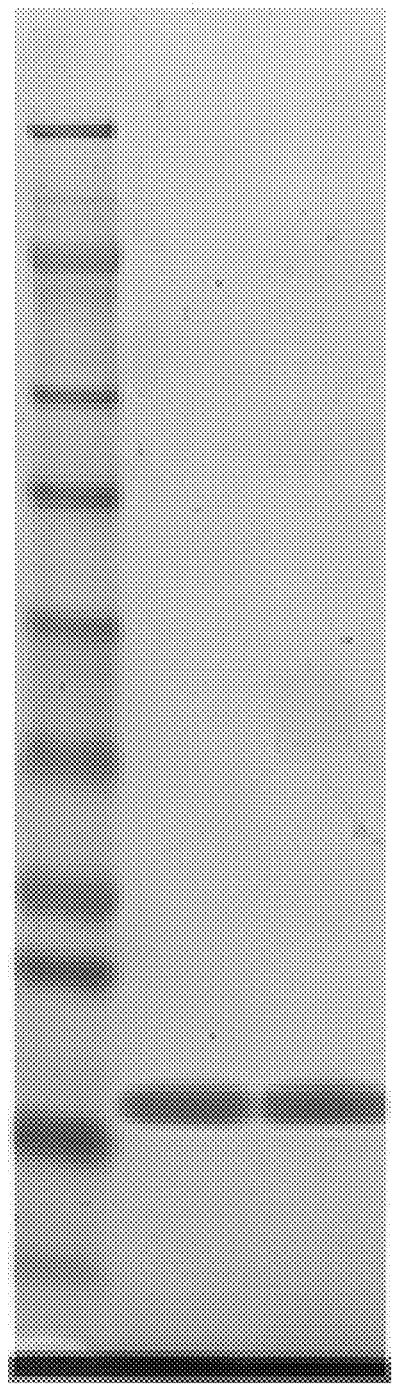
FIG. 1. SDS-PAGE analysis of purified Tencon performed on a NuPAGE 4-12% Bis-Tris gel (Invitrogen) and stained with coomassie blue. N stands for native conditions and R for reduced conditions.

Protein concentration was determined using a BioTek plate reader to measure the absorbance of the sample at 280 nm. The final preparation was analyzed by Coomassie stain (FIG. 1), Western blot with anti-His antibody, and by HPLC-SEC using a G3000SW-XL column (TOSOH Biosciences) equilibrated in PBS. SDS-PAGE analysis shows that Tencon migrates between 6 and 14 kDa, in agreement with the expected mass of 10.7 kDa for the monomeric protein. A yield of >50 mg of pure Tencon protein per liter of culture was obtained.

Biophysical Characterization

Figure 2:
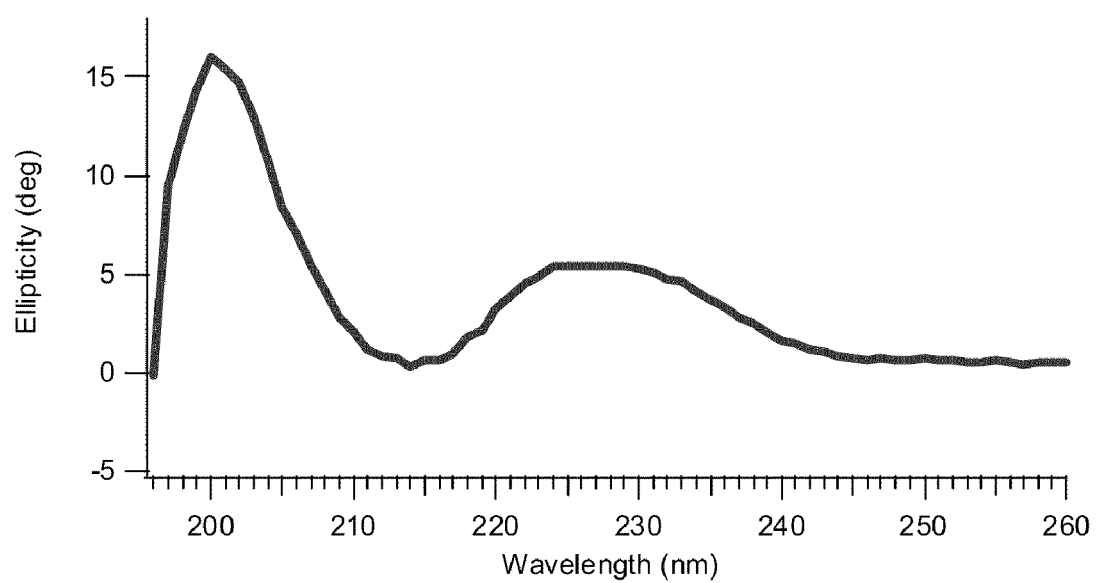
FIG. 2. Circular dichroism analysis of Tencon in PBS.
Figure 3:
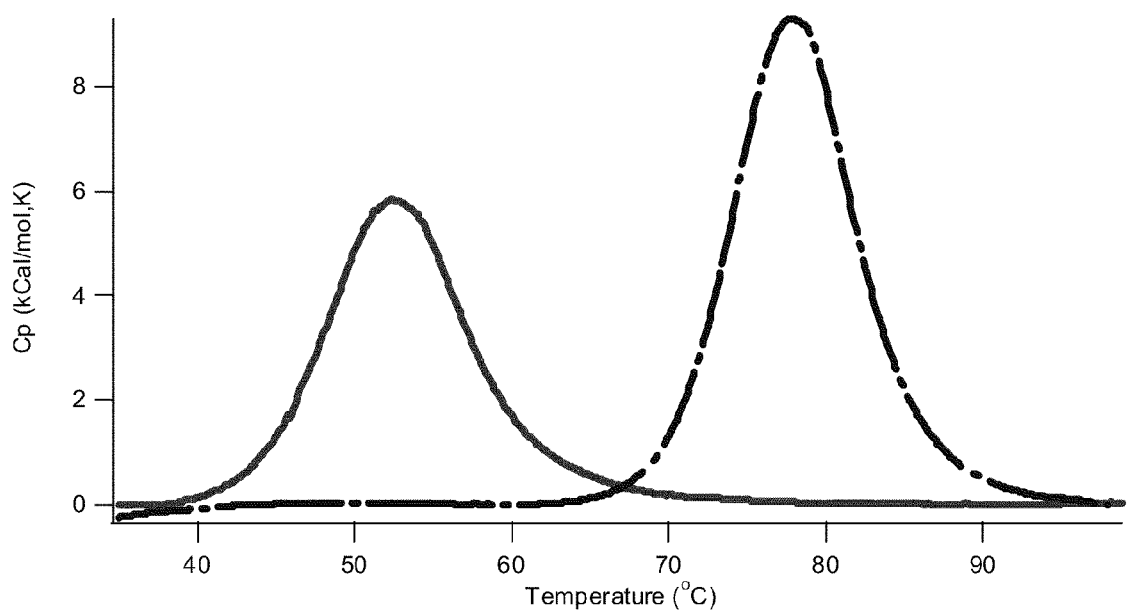
FIG. 3. DSC analysis of the $3^{rd}$ FN3 domain from Tenascin and Tencon in PBS. Melting temperatures of 54° C. and 78° C. were obtained respectively.

The structure and stability of Tencon was characterized by circular dichroism spectroscopy and differential scanning calorimetry respectively. CD measurements were made on an AVIV spectrometer at 20° C. in PBS and a concentration of 0.2 mg/mL. The spectrum in FIG. 2 shows a minimum at 218 nm, suggestive of β-sheet structure as expected for a protein belonging to the FN3 family as designed. DSC data was obtained by heating 0.5 mg/mL solutions of the $3^{rd}$ FN3 domain from Tenascin or Tencon in PBS from 35° C. to 95° C. at a rate of 1° C./minute in an N-DSCII calorimeter (Applied Thermodynamics). A buffer only curve was subtracted to produce the profiles shown in FIG. 3. From this data, melting temperatures of 54° C. and 78° C. were calculated for the $3^{rd}$ FN3 domain and Tencon, respectively, using CpCalc (Applied Thermodynamics) software. The folding and unfolding of both domains is reversible at these temperatures.

Immunogenicity Analysis

A computer program that models for immunogenicity to human of amino acid sequences was used to compare the predicted immunogenicity of amino acid sequences representing the $3^{rd}$ FN3 domain of human Tenascin, Tencon, and several therapeutic antibodies (shown in Table 2). Chimeric mAbs and a human mAb (adalimumab) analyzed with the program were followed by application of a tolerance threshold (removes 9-mer peptides with 100% identity to human germline encoded sequence). The tolerance threshold was not applied to Tenascin or Tencon. The tolerance threshold assumes broad T cell tolerance to germline encoded mAb sequences and focuses analyses on novel sequence primarily in CDRs and flanking domains.

These analyses predict a low immunogenic risk for both Tenascin and Tencon based on the likelihood that a 9-mer peptide, derived from the analyzed sequence will bind one or more HLA molecules. The score is weighted with respect to the prevalence of each HLA allele. The scores for the models were summed for each sequence to provide a single number describing the overall PIR of each sequence (score sum). The results from this analysis are summarized in Table 2. Tenascin was shown to have the lowest overall Score (11.9). Tencon, like Tenascin, scored primarily non-binders and low predicted immunogenic risk agretopes (Score=13.2). The Tenascin and Tencon sequences scored favorably as compared to the therapeutic antibodies.

Display of Tencon on M13 Phage by pIX Fusion

Figure 4:
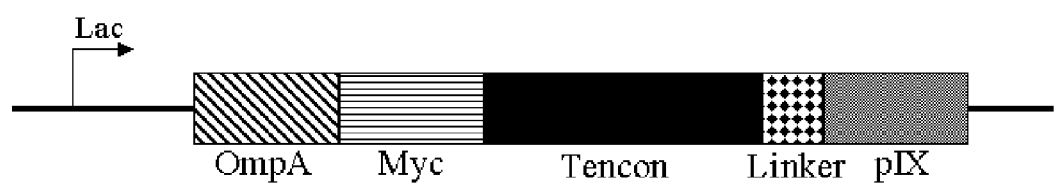
FIG. 4. Phagemid plasmid design of pTencon-pIX. Expression is driven by a Lac promoter and secretion via the OmpA signal sequence.

The gene encoding the Tencon amino acid sequence was subcloned into the phagemid expression vector pPep9 by PCR and restriction digest cloning, resulting in the vector pTencon-pIX. This system expresses N-terminally Myc-tagged Tencon as a C-terminal fusion to the N-terminus of the M13 pIX protein (FIG. 4). The Lac promoter allows for lower levels of expression without IPTG and increased expression after the addition of IPTG. The OmpA signal sequence was appended to the N-terminus of Tencon to promote efficient translocation to the periplasm. A short TSGGGGS linker (SEQ ID NO: 141) was constructed between Tencon and pIX to prevent steric interactions between these proteins.

For confirmation of display on the surface of the M13 phage particle, pTencon-pIX was transformed into XL1-Blue *E. coli* and a single colony was used to innocualte a 5 ml, LB culture supplemented with ampicillin. This culture was grown at 37° C. until reaching mid-log phase at which point $6^{10}$ pfu of VCSM13 helper phage was added and the culture incubated at 37° C. for 10 minutes without shaking followed by 50 minutes with shaking. The helper phage rescued culture was then diluted into 50 mL of 2YT media supplemented with ampicillin and kanamycin and grown at 37° C. with shaking until O.D.$_{600}$ reached 0.7, at which point IPTG was added to a final concentration of 1 mM and the temperature reduced to 30° C. After 16 hours, the culture was centrifuged at 4000×g for 20 minutes and the supernatant collected and stored at 4° C. for analysis.

Figure 5:
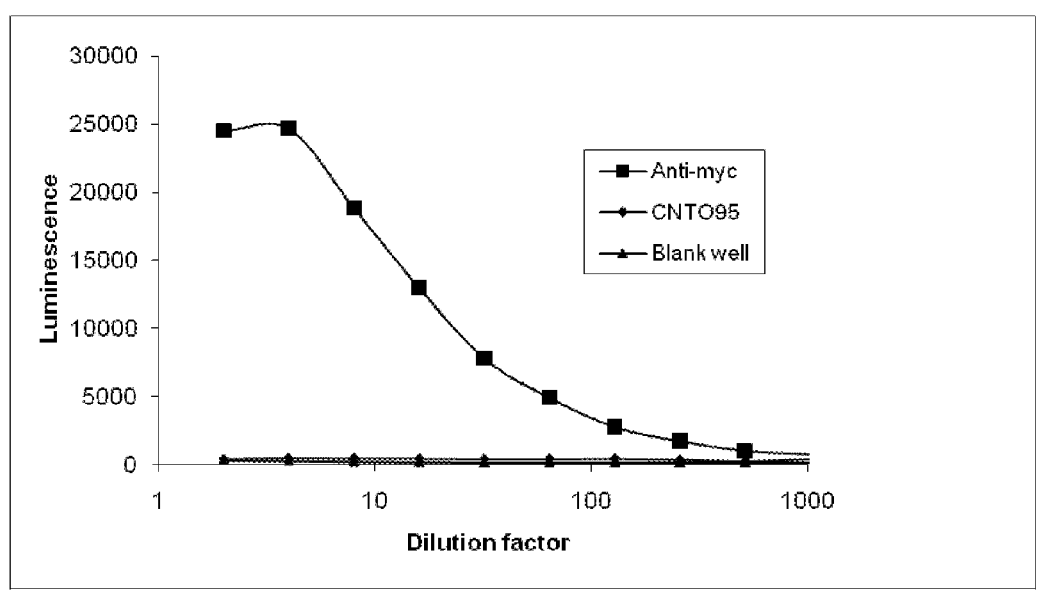
FIG. 5. Display of Myc-Tencon on M13 phage. ELISA results showing binding of phage to α-Myc coated, CNTO95 coated, and uncoated wells.

Binding of the phage particles to an anti-Myc antibody (Invitrogen) was used to confirm the display of the Myc-Tencon construct on the M13 phage surface. A Maxisorp plate was coated overnight at a concentration of 2.5 µg/mL with α-Myc or an anti-αv antibody (negative control) and blocked with SuperBlock T20 (Pierce). Two-fold serial dilutions of the phagemid culture supernatant described above were made in PBS and added to the wells of the coated plate. After 1 hour, the plate was washed with TBST and a α-M13 HRP antibody was added to each well and washed with TBST following a 1-hour incubation. The Roche BD ELISA POD substrate was added and luminescence detected on a plate reader (Tecan). FIG. 5 shows that the Myc-Tencon phage particles bind to the α-myc, but not the anti-αv antibody coated wells or the uncoated control wells of the plate in a concentration dependent manner, confirming the specific display of Myc-Tencon on the M13 phage particle.

An additional phagemid vector can be constructed to display Tencon and library members (see Example 2) on M13 phage as fusions to coat protein pIII. For this system, the gene for pIX is replaced with a gene encoding a truncated version of pIII (Bass et al. 1990). Additional changes as compared to the system shown in FIG. 4 include the replacement of the OmpA signal sequence with the signal sequence for DsbA, as secretion using this sequence has been shown to be beneficial for the display of stable alternative scaffold molecules (Steiner et al. 2006).

Example 2

Generation of Tencon Libraries

Tencon variant libraries can be made by many different methods, depending on the desired complexity and the relative location of mutations in the molecule. DNA synthesis methods are preferred to create mutations scattered throughout the Tencon gene. Restriction enzyme cloning can also be used to recombine DNA fragments containing mutations in different regions of the gene. Saturating mutagenesis in a small-defined region, such as a single Tencon loop, can be introduced by using a degenerate oligo-nucleotide and oligo-nucleotide directed mutagenesis (Kunkel et al. 1987).

A Tencon library, library FG7, designed to replace the FG loop with 7 random amino acids using oligonucleotide directed mutagenesis was constructed. An oligonucleotide (TconFG7-For-5' pho) was synthesized to have a 21 base pair (bp) degenerate sequence of NNS at the positions encoding the FG loop and two flanking 20-27 bp nucleotide sequences of complementarity to the Tencon coding sequence. In this design, all twenty amino acids are capable of being represented in the FG loop. The calculated diversity at nucleotide level is 1.3×10$^9$.

TconFG7-For5'pho:

(SEQ ID NO: 18)
GAATACACCGTTTCTATCTACGGTGTTNNSNNSNNSNNSNNSNNSNNSCC
GCTGTCTGCGGAATTCAC

The template for oligonucleotide directed mutagenesis, pDsbA-Tencon-Asc-loop-Myc-pIII, was constructed by replacing the Tencon F:G loop encoding sequence with a stem loop sequence containing an AscI restriction site. This system allows the elimination of background template DNA after mutagenesis by digesting the resulting DNA with AscI prior to transformation. To purify a single-stranded DNA template for mutagenesis, a single colony of *E. coli* CJ236 harboring pDsbA-Tencon-Asc-loop-Myc-pIII, was picked into 5 mL of 2YT growth medium with carbenicillin (50 µg/ml final concentration) and Chloramphenicol (10 µg/ml). After 6 hours, VCSM13 helper phage was added to a final concentration of $10^{10}$ pfu/ml and incubated without shaking for 10 minutes before being transferred to 150 mL of 2YT with carbenicillin (10 µg/ml) and uridine (0.25 µg/ml) and incubated at 37° C. with shaking at 200 rpm overnight. The cells were pelleted by centrifugation and the supernatant collected and the phage pelleted with PEG NaCl. Single strand DNA was purified from this pellet using a QIAprep Spin M13 kit (Qiagen) according to the manufacturer instructions.

To anneal the degenerate oligonucleotide to the template, 5 µg of template DNA was combined with oligo TconFG7-For-5-pho at a molar ratio of 10:1 in Tris-HCl (50 mM, pH7.5) and MgCl2 (10 mM) and incubated at 90° C. for 2 minutes, 60° C. for 3 minutes, and 20° C. for 5 minutes. After the annealing reaction, ATP (10 mM), dNTPs (25 mM each), DTT (100 mM), T4 ligase (7 units), and T7 DNA polymerase (10 units) were added to the reaction mixture and incubated at 14° C. for 6 hours followed by 20° C. for 12 hours. The resulting DNA was purified using a PCR purification kit (Qiagen) and recovered in 100 µL of water. The library DNA was digested with 10 units of AscI for 4 hours and then purified again with Qiagen PCR purification kit. The final library DNA was recovered in 50 µL of water. The resulting double stranded DNA product was then transformed into into *E. coli* MC1061F' by electroporation.

The transformants were collected in 20 mL SOC medium and allowed to recover for 1 hour at 37° C. At the end of the recovery, an aliquot of the transformation was serial diluted and plated on Carbenicillin (100 ug/ml) plates containing 1% glucose to assess the total transformant number. The remaining SOC culture was then used to inoculate 1 L of 2xYT medium with Carbinicillin and 1% glucose and grown until OD$_{600}$ reached 0.6. 100 mL of this culture was inoculated with M13 helper phage to $10^{10}$/mL and incubated at 37° C. before centrifugation. The resulting cell pellet was resuspended in 500 mL fresh 2xYT medium containing Carbenicillin (100 ug/mL) and Kanamycin (35 ug/mL) and grown at 30° C. overnight before centrifugation. Phage particles were precipitated by the addition of PEG/NaCl and stored at −80° C.

A second library, BC6/FG7, was designed to introduce diversity within the B:C and F:G loops of Tencon simultaneously. In order to do so, two oligonucleotides, Tc-BC6-For-5' phos and POP149 were synthesized. The forward oligo was phosphorylated and contained 18 bases of NNS codon at each position encoding the B:C loop, while the reverse oligo was biotinylated at the 5' end and contained 21 bases of NNS codon at each position encoding the F:G loop. Both oligonucleotides are flanked by two 18 bp nucleotide sequences identical to the region preceding and following the region to be mutagenized (see below for primer detail).

Tc-BC6-For-5'phos:
(SEQ ID NO: 19)
gactctctgcgtctgtcttggNNSNNSNNSNNSNNSNNSNNSTTCGACTCTTT
CCTGATCCAGTACC POP 2149:
(SEQ ID NO: 20)
GTGAATTCCGCAGACAGCGGSNNSNNSNNSNNSNNSNNSNNAACACCGTA
GATAGAAACGGTG To construct the library, sixteen 100 µL PCR reactions were performed using t oligos Tc-CB6-For5'phos and POP2149 to amplify the Tencon DNA template, introducing NNS codons into the B:C and F:G loops simultaneously in the process. The double-stranded PCR product was mixed with magnetic streptavidin beads (Dynal) in B&W buffer (10 mM Tris-HCl, pH7.5, 1 mM EDTA, 2M NaCl, 0.1% Tween-20) and incubated for 20 minutes, pulled down with a magnet and washed with B&W buffer twice. The forward strand was eluted from the beads with 300 µL of 150 mM NaOH. This "megaprimer," a mixture of long primers with more than $8 \times 10^{16}$ in theoretical diversity, was used to anneal to a single strand library template. Library construction was carried out as described above for the FG7 library.

Example 3

Selection of IgG Binders

In order to perform selections of Tencon library members that bind to IgG, recombinant IgG (human IgG1 subtype) was biotinylated using sulfo-NHS-LC-Biotin (Pierce) before dialyzing into PBS. For selections, 200 µL of phage displaying libraries FG7 or BC6/FG7 were blocked with 200 µL of chemiblocker before the addition of biotinylated IgG at concentrations of 500 nM (round 1) or 100 nM (rounds 2 and 3). Bound phages were recovered by Neutravidin magnetic beads (Seradyne) in round 1 or streptavidin magnetic beads (Promega) in rounds 2 and 3. Unbound phages were washed from the beads using 5-10 washes with 1 mL of Tris buffered saline with tween (TBST) followed by 2 1 mL washes with Tris buffered saline (TBS). Bound phages were eluted from the beads by the addition of mid-log phase E. coli MC1061F'. Infected cells were plated on LB agar plates supplemented with carbenicillin and glucose. The next day, cells were scraped from the plate and grown to mid-log phase before rescue with VCSM13 helper phage and grown overnight. Phage particles isolated by PEG/NaCl precipitation and used for the next round of selections.

After 3 rounds of panning against IgG, the output was subcloned into a pET27 vector modified to include a ligase independent cloning site by amplifying the Tencon gene by PCR. This PCR product was annealed to the vector and transformed into BL21-GOLD(DE3) cells (Stratagene). Individual colonies were picked into 1 mL cultures in 96 deep well plates (Corning) and grown to saturation overnight at 37° C. The next day, 50 µL of the overnight culture was used to inoculate a fresh 1 mL culture. Cultures were grown at 37° C. for 2 hours before adding IPTG to 1 mM and reducing the temperature to 30° C. Cells were harvested by centrifugation 16 hours after induction and lysed with 100 µL of BugBuster (Novagen). The resulting lysates were clarified by centriguation and used to test for binding to IgG by ELISA.

Figure 7:
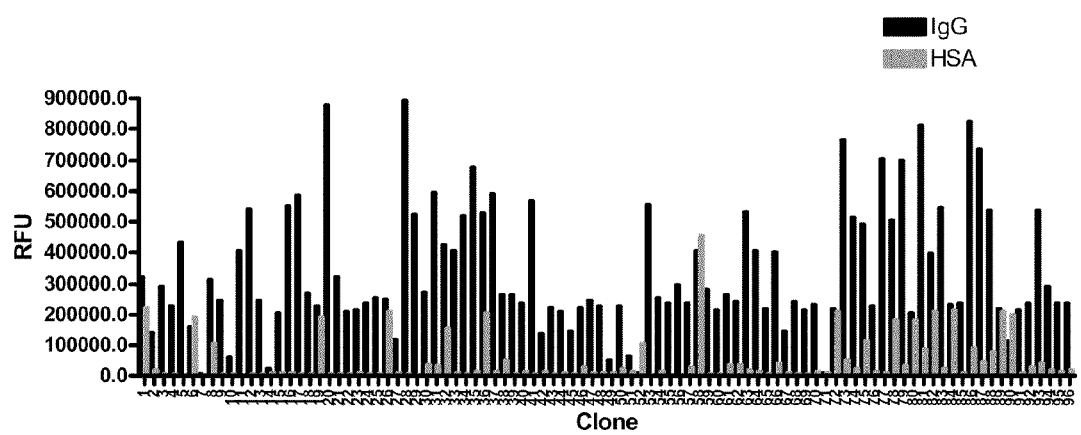
FIG. 7. Screening of output of IgG selections by ELISA. Individual clones were tested for binding to biotinylated IgG or biotinylated HSA as a control.

Maxisorp plates (Nunc) were coated with 0.1 µg of anti-HIS antibody (Qiagen) overnight, washed with TBST, and blocked with Starting Block T20 (Thermo Scientific). Clarified lysates diluted 1:4 in Starting Block were added to the plates and allowed to bind for 1 hour before washing with TBST. Biotinylated IgG or biotinylated HSA was added at a concentration of 1 µg/ml and washed with TBST after a 1 hour incubation. Detection of bound IgG or HSA was accomplished by adding streptavidin-HRP (Jackson Immunoresearch) and detecting with POD chemiluminescence substrate. Results of the ELISA are shown in FIG. 7. Constructs that bound biotinylated IgG more than 10-fold over biotinylated HSA as judged by ELISA signal were sequenced. After completion of several selection experiments, 60 unique binding sequences from library FG7 and 10 unique sequences from library BC6FG7 were obtained; Table 4 shows representative sequences of IgG binders in which the B:C and/or F:G loops are shown to the extent they are different than those of SEQ ID NO:16. Also shown in Table 4 are numerous mutations in other regions of the scaffold.

The Tencon protein designed, expressed, and purified here has a thermal stability improved by 26° C. with respect to that of the $3^{rd}$ FN3 domain from human Tenascin, which has been used as an alternative scaffold molecule. Based on this stability increase, this scaffold molecule is likely to be more amenable to amino acid substitution and easier to manufacture. Mutations that decrease protein stability are likely to be better tolerated in the context of a more stable scaffold and thus a scaffold with enhanced stability is likely to yield more functional, well folded binders from a library of scaffold variants. As this novel protein is not a protein encoded by the human genome, it may also provide less risk toward the generation of an immune response than the risk against, for example, native human Tenascin when used as a therapeutic (essentially, less risk than with a therapeutic based on the wild type domain).

For the purposes of this invention, 70-100% amino acid or nucleotide sequence identity (i.e., 90, 91, 92, 93, 94, 95, 96, 97, 98, 99, 100 or any range or value therein) is determined using a suitable computer algorithm, as known in the art.

It will be clear that the invention can be practiced otherwise than as particularly described in the foregoing description and examples. Numerous modifications and variations of the present invention are possible in light of the above teachings and, therefore, are within the scope of the appended claims.

TABLE 1

|     | (1) 1 | \|10 | \|20 | \|30 | \|40 | \|50 | \|60 |
| --- | --- | --- | --- | --- | --- | --- | --- |
| 1 (1) | ---SPPKDLVVTEVTEETVNLAWDN-EMRVTEYLVVYTPTH--EGGLEMQFRVPGDQTSTI | | | | | | |
| 2 (1) | TYLPAPEGLKFKSIKETSVEVEWDPLDIAFETWEIIFRNMN-KEDEGEITKSLRRPETSYR | | | | | | |
| 3 (1) | ---DAPSQIEVKDVTDTTALITWFKPLAEIDGIELTYGIKD--VPGDRTTIDLTEDENQYS | | | | | | |
| 4 (1) | TGLDAPRNLRRVSQTDNSITLEWRNGKAAIDSYRIKYAPISGGDHAEVDVPKSQQATTKTT | | | | | | |

TABLE 1-continued

```
 5 (1) ---DTPKDLQVSETAETSLTLLWKTPLAKFDRYRLNYSLPT----GQWVGVQLPRNTTSYV
 6 (1) -QAPELENLTVTEVGWDGLRLNWTAADQAYEHFIIQVQEAN--KVEAARNLTVPGSLRAVD
 7 (1) -ETPNLGEVVVAEVGWDALKLNWTAPEGAYEYFFIQVQEAD--TVEAAQNLTVPGGLRSTD
 8 (1) -EVPDMGNLTVTEVSWDALRLNWTTPDGTYDQFTIQVQEAD--QVEEAHNLTVPGSLRSME
 9 (1) -DLPQLGDLAVSEVGWDGLRLNWTAADNAYEHFVIQVQEVN--KVEAAQNLTLPGSLRAVD
10 (1) -KEPEIGNLNVSDIPPESFNLSWMATDGIFETFTIEIIDSN--RLLETVEYNISGAERTAH
11 (1) -ALPLLENLTISDINPYGFTVSWMASENAFDSFLVTVVDSG--KLLDPQEFTLSGTQRKLE
12 (1) -AEPEVDNLLVSDATPDGFRLSWTADEGVFDNFVLKIRDTK--KQSEPLEITLLAPERTRD
13 (1) ---GSPKEVIFSDITENSATVSWRAPTAQVESFRITYVPITG---GTPSMVTVDGTKTQTR
14 (1) ---DGPSGLVTANITDSEALARWQPAIATVDSYVISYTGEK----VPEITRTVSGNTVEYA
15 (1) ---DSPRDLTATEVQSETALLTWRPPRASVTGYLLVYESVD----GTVKEVIVGPDTTSYS (1)      |70       |80       |90       |100
             1 (1) IQELEPGVEYFIRVFAILENKKSIPVSARVAT-------
             2 (1) QTGLAPGQEYEISLHIVKNNTRGPGLKRVTTTRLD----
             3 (1) IGNLKPDTEYEVSLISRRGDMSSNPAKETFTT-------
             4 (1) LTGLRPGTEYGIGVSAVKEDKESNPATINAATELDTPKD
             5 (1) LRGLEPGQEYNVLLTAEKGRHKSKPAKSKPARVK-----
             6 (1) IPGLKAATPYTVSIYGVIQGYRTPVLSAEASTGE-----
             7 (1) LPGLKAATHYTITIRGVTQDFSTTPLSVEVLTE------
             8 (1) IPGLRAGTPYTVTLHGEVRGHSTRPLAVEVVTE------
             9 (1) IPGLEAATPYRVSIYGVIRGYRTPVLSAEASTAKEPE--
            10 (1) ISGLPPSTDFIVYLSGLAPSIRTKTISATATTE------
            11 (1) LRGLITGIGYEVMVSGFTQGHQTKPLRAEIVTE------
            12 (1) LTGLREATEYEIELYGISKGRRSQTVSAIATTAM-----
            13 (1) LVKLIPGVEYLVSIIAMKGFEESEPVSGSFTTAL-----
            14 (1) LTDLEPATEYTLRIFAEKGPQKSSTITAKFTTDL-----
            15 (1) LADLSPSTHYTAKIQALNGPLRSNMIQTIFTTIGL----
```

TABLE 2

| Sequence | Description | | 1st Score sum | 2nd Score sum | Score sum (chain) | Score sum (molecule) |
|---|---|---|---|---|---|---|
| Tenascin | Alt. Scaff. | | 6.01 | 5.85 | 11.86 | 11.86 |
| Tencon | Alt. Scaff. | | 5.83 | 7.37 | 13.20 | 13.20 |
| adalimumab | humanized mAb | Vh | 9.45 | 8.06 | 17.50 | 45.42 |
|  |  | Vl | 15.29 | 12.63 | 27.92 |  |
| cetuximab | Chimeric mAb | Vh | 17.63 | 16.89 | 34.52 | 64.44 |
|  |  | Vl | 14.45 | 15.47 | 29.92 |  |
| Rituximab | Chimeric mAb | Vh | 16.57 | 14.38 | 30.96 | 61.65 |
|  |  | Vl | 16.63 | 14.06 | 30.69 |  |
| basiliximab | Chimeric mAb | Vh | 16.48 | 13.40 | 29.89 | 58.98 |
|  |  | Vl | 16.05 | 13.05 | 29.09 |  |

Sequences:

SEQ ID No. 1:
sppkdlvvtevteetvnlawdnemrvteylvvytptheggIemqfrvpgd
qtstiiqelepgveyfirvfailenkksipvsarvat SEQ ID No. 2:
tylpapeglkfksiketsvevewdpldiafetweiifrnmnkedegeitk
slrrpetsyrqtglapgqeyeislhivknntrgpglkrvttrld SEQ ID No. 3:
dapsqievkdvtdttalitwfkplaeidgieltygikdvpgdrttidlte
denqysignlkpdteyevslisrrgdmssnpaketfttt SEQ ID No. 4
tgldaprnlrrvsqtdnsitlewrngkaaidsyrikyapisggdhaevdv
pksqqattkttltglrpgteygigvsavkedkesnpatinaateldtpkd SEQ ID No. 5
dtpkdlqvsetaetsltllwktplakfdryrlnyslptgqwvgvqlprnt
tsyvlrglepgqeynvlltaekgrhkskpakskparvk -continued SEQ ID No. 6
qapelenltvtevgwdglrlnwtaadqayehfiiqvqeankveaarnltv
pgslravdipglkaatpytvsiygviqgyrtpvlsaeastge SEQ ID No. 7
etpnlgevvvaevgwdalklnwtapegayeyffiqvqeadtveaaqnltv
pgglrstdlpglkaathytitirgvtqdfsttplsvevlte SEQ ID No. 8
evpdmgnltvtevswdalrlnwttpdgtydqftiqvqeadqveeahnltv
pgslrsmeipglragtpytvtlhgevrghstrplavevvte SEQ ID No. 9
dlpqlgdlavsevgwdglrlnwtaadnayehfviqvqevnkveaaqnltl
pgslravdipgleaatpyrvsiygvirgyrtpvlsaeastakepe SEQ ID No. 10
kepeignlnvsditpesfnlswmatdgifetftieiidsnrlletveyni
sgaertahisglppstdfivylsglapsirtktisatatte SEQ ID No. 11
alpllenltisdinpygftvswmasenafdsflvtvvdsgklldpqeftl
sgtqrklelrglitgigyevmvsgftqghqtkplraeivte SEQ ID No. 12
aepevdnllvsdatpdgfrlswtadegvfdnfvlkirdtkkqsepleitl
lapertrdltglreateyeielygiskgrrsqtvsaiattam SEQ ID No. 13
gspkevifsditensatvswraptaqvesfrityvpitggtpsmvtvdgt
ktqtrlvklipgveylvsiiamkgfeesepvsgsfttal SEQ ID No. 14
dgpsglvtanitdsealarwqpaiatvdsyvisytgekvpeitrtvsgnt
veyaltdlepateytlrifaekgpqksstitakfttdl SEQ ID No. 15
dsprdltatevqsetalltwrpprasvtgyllvyesvdgtvkevivgpdt
tsysladlspsthytakiqalngplrsnmiqtiftttigl SEQ ID No. 16
LPAPKNLVVSEVTEDSLRLSWTAPDAAFDSFLIQYQESEKVGEAINLTVP
GSERSYDLTGLKPGTEYTVSIYGVKGGHRSNPLSAEFTT SEQ ID No. 17
ctgccggcgccgaaaaacctggttgtttctgaagttaccgaagactctct
gcgtctgtcttggaccgcgccggacgcggcgttcgactcttttcctgatcc
agtaccaggaatctgaaaaagttggtgaagcgatcaacctgaccgttccg
ggttctgaacgttcttacgacctgaccggtctgaaaccgggtaccgaata
caccgtttctatctacggtgttaaaggtggtcaccgttctaacccgctgt
ctgcggaattcaccacc Tencon Sequence Showing Loops (SEQ ID NO:16)

TABLE 3

Loops of Tencon

| Loop | Residues of SEQ ID NO: 16 | Amino Acid Sequence |
|---|---|---|
| A-B | 13-16 | TEDS |
| B-C | 22-28 | TAPDAAF |
| C-D | 38-43 | SEKVGE |
| D-E | 51-54 | GSER |
| E-F | 60-64 | GLKPG |
| F-G | 75-81 | KGGHRSN |

```
           A-B loop    B-C loop        C-D loop
1-LPAPKNLVVSEVTEDSLRLSWTAPDAAFDSFLIQYQESEKVGEA D-E loop   E-F loop   F-G loop
INLTVPGSERSYDLTGLKPGTEYTVSIYGVKGGHRSNPLSAEFTT-89
```

TABLE 4

Scaffolds binding to IgG

| Clone No. | B:C Loop Residues 22-28 (SEQ ID NO) | F:G Loop Residues 75-81 (SEQ ID NO) | Scaffold Mutations |
|---|---|---|---|
| 1 | SYGFNN (21) | QIGPIIP (46) | |
| 2 | TYEGES (22) | QIGPIIP (46) | |
| 3 | TYESES (23) | QIGPIIP (46) | |
| 4 | TNWMDS (24) | SIRTIDS (47) | |
| 5 | KSVFIM (25) | PKFHSPL (48) | |
| 6 | YSSYAT (26) | WKTTIWF (49) | |
| 7 | RFHPFP (27) | RKNWKTR (50) | |
| 8 | MMCMPL (28) | RLFRIYQ (51) | |
| 9 | YCRVRD (29) | WLSRSYD (52) | |
| 10 | SYGFNN (21) | WLSRSYD (52) | |
| 11 | MDCFMG (30) | WLSRSCD (53) | |
| 12 | TYRFNS (31) | WMGPYCD (54) | |
| 13 | ASRRSL (32) | RRRRYSF (55) | |
| 14 | TIESES (33) | HIVPMVP (56) | |
| 15 | TL*MQS (34) | QIEPIIR (57) | |
| 16 | IYDSES (35) | PSAANNP (58) | |
| 17 | | VRLRYVQ (59) | |
| 18 | | QVGPLIP (60) | |
| 19 | | RIGPILP (61) | |
| 20 | | QIGPLLP (62) | |
| 21 | | RIGPLLP (63) | |
| 22 | | QVGPLLP (64) | |
| 23 | | RIGPMLP (65) | |
| 24 | | QIGPVLP (66) | |
| 25 | | RIGPVLP (67) | |
| 26 | | QIGPMMP (68) | |
| 27 | | QVGPLVP (69) | |
| 28 | | QIGPMLP (70) | R18P |
| 29 | | QVGPILP (71) | |
| 30 | | QVGPLLP (64) | |
| 31 | | QVGPMLP (72) | |
| 32 | | QIGPIVP (73) | I33V |
| 33 | | MIGPLLP (74) | |
| 34 | | QIGPLFP (75) | |
| 35 | | QIGPVLP (66) | T59A |
| 36 | | QIGPMVP (76) | |
| 37 | | QIGPIVP (77) | |

TABLE 4-continued

Scaffolds binding to IgG

| Clone No. | B:C Loop Residues 22-28 (SEQ ID NO) | F:G Loop Residues 75-81 (SEQ ID NO) | Scaffold Mutations |
|---|---|---|---|
| 38 | | RIEPILP (78) | V74G |
| 39 | | VAGSVWP (79) | |
| 40 | | REGATLY (80) | |
| 41 | | KQIPPIL (81) | S38G |
| 42 | | LSLSSVL (82) | |
| 43 | | HMLLPLP (83) | V74A |
| 44 | | MIGPLIP (84) | |
| 45 | | TIGPHIP (85) | |
| 46 | | EIGPCLP (86) | |
| 47 | | EIGPVLP (87) | |
| 48 | | KIGPCLP (88) | Y35H |
| 49 | | MIGPVLP (89) | |
| 50 | | QIGPILP (90) | S52P |
| 51 | | QIGPILP (90) | Q36R |
| 52 | | QIGPILP (90) | |
| 53 | | EVGPILP (91) | |
| 54 | | QVGPLLP (92) | A23T |
| 55 | | QIGPVMP (93) | |
| 56 | | QIGPCVP (94) | |
| 57 | | QIGPLVP (95) | |
| 58 | | RGLVMPM (96) | V74A |
| 59 | | MIGPILP (97) | |
| 60 | | QIGPILP (90) | E37G |
| 61 | | QIGPILP (90) | T68A |
| 62 | | QIGPILP (90) | T22I |
| 63 | | QIGPILP (90) | S52F |
| 64 | | QIGPILP (90) | Y56H |
| 65 | | QIGPILP (90) | A44V |
| 66 | | QIGPILP (90) | P24S |
| 67 | | RIGPILP (61) | |
| 68 | | CIGPMVP (98) | |
| 69 | | FIGPVLP (99) | |
| 70 | | HIGPILP (100) | |
| 71 | | HIGPIMP (101) | |
| 72 | | HIGPYLP (102) | |
| 73 | | HVGPILP (103) | |
| 74 | | IIGPLLP (104) | |
| 75 | | LIGPLLP (105) | |
| 76 | | MVGPLLP (106) | |
| 77 | | NIGPYLP (107) | |
| 78 | | NIGPYLP (108) | |
| 79 | | QIGPHLP (109) | |
| 80 | | QIGPIIP (46) | |
| 82 | | QIGPILG (110) | |
| 83 | | QIGPILS (111) | |
| 83 | | QIGPILT (112) | |
| 84 | | QIGPIMP (113) | |
| 85 | | QIGPIPI (114) | |
| 86 | | QIGPLLN (115) | |
| 87 | | QIGPLLP (62) | |
| 88 | | QIGPVFP (116) | |
| 89 | | QIGPVLS (117) | |
| 90 | | QIGPWLP (118) | |
| 92 | | QVGPILP (71) | |
| 93 | | QVGPILR (118) | |
| 94 | | QVGPIMN (119) | |
| 95 | | QVGPIMP (120) | |
| 96 | | QVGPIVP (121) | |
| 97 | | QVGPLLS (122) | |
| 98 | | QVGPVLP (123) | |
| 99 | | QVGPVLT (124) | |
| 100 | | RIGPIMP (125) | |
| 101 | | RIGPIVP (126) | |
| 102 | | RIGPMFP (127) | |
| 103 | | RIGPMIP (128) | |
| 104 | | RIGPMVP (129) | |
| 105 | | RIGPVIP (130) | |
| 106 | | RVGPILP (131) | |
| 107 | | RVGPLLP (132) | |
| 108 | | TVGPHIP (133) | |
| 109 | DRKRFI (36) | PSWRSNW (134) | |
| 110 | EFWRGS (37) | QIGPLLP (62) | |
| 111 | GLLDPL (38) | ALRATLE (135) | |
| 112 | GLVLPE (39) | KYGYLTP (136) | |

TABLE 4-continued

Scaffolds binding to IgG

| Clone No. | B:C Loop Residues 22-28 (SEQ ID NO) | F:G Loop Residues 75-81 (SEQ ID NO) | Scaffold Mutations |
|---|---|---|---|
| 113 | MASDGL (40) | RIGPMLP (137) | |
| 114 | NKTETN (41) | NPFCSRF (138) | |
| 115 | QAERKV (42) | QIGPLLP (62) | |
| 116 | QAERKV (42) | RIGPLLP (63) | |
| 117 | SQVCTL (43) | YYLHQWC (139) | |
| 118 | YFDKDS (44) | QIGPLLP (62) | |
| 119 | YFECEP (45) | HIVPLLR (140) | |

What is claimed is:

1. An isolated protein scaffold, comprising the amino acid sequence of SEQ ID NO:16.

* * * * *

SEQUENCE LISTING

<160> NUMBER OF SEQ ID NOS: 141

<210> SEQ ID NO 1
<211> LENGTH: 87
<212> TYPE: PRT
<213> ORGANISM: Homo sapiens

<400> SEQUENCE: 1

Ser Pro Pro Lys Asp Leu Val Val Thr Glu Val Thr Glu Glu Thr Val
 1               5                  10                  15

Asn Leu Ala Trp Asp Asn Glu Met Arg Val Thr Glu Tyr Leu Val Val
            20                  25                  30

Tyr Thr Pro Thr His Glu Gly Gly Leu Glu Met Gln Phe Arg Val Pro
        35                  40                  45

Gly Asp Gln Thr Ser Thr Ile Ile Gln Glu Leu Glu Pro Gly Val Glu
    50                  55                  60

Tyr Phe Ile Arg Val Phe Ala Ile Leu Glu Asn Lys Lys Ser Ile Pro
65                  70                  75                  80

Val Ser Ala Arg Val Ala Thr
                85

<210> SEQ ID NO 2
<211> LENGTH: 95
<212> TYPE: PRT
<213> ORGANISM: Homo sapiens

<400> SEQUENCE: 2

Thr Tyr Leu Pro Ala Pro Glu Gly Leu Lys Phe Lys Ser Ile Lys Glu
 1               5                  10                  15

Thr Ser Val Glu Val Glu Trp Asp Pro Leu Asp Ile Ala Phe Glu Thr
            20                  25                  30

Trp Glu Ile Ile Phe Arg Asn Met Asn Lys Glu Asp Glu Gly Glu Ile
        35                  40                  45

Thr Lys Ser Leu Arg Arg Pro Glu Thr Ser Tyr Arg Gln Thr Gly Leu
    50                  55                  60

Ala Pro Gly Gln Glu Tyr Glu Ile Ser Leu His Ile Val Lys Asn Asn
65                  70                  75                  80

Thr Arg Gly Pro Gly Leu Lys Arg Val Thr Thr Thr Arg Leu Asp
                85                  90                  95

<210> SEQ ID NO 3
<211> LENGTH: 88
<212> TYPE: PRT
<213> ORGANISM: Homo sapiens

<400> SEQUENCE: 3

Asp Ala Pro Ser Gln Ile Glu Val Lys Asp Val Thr Asp Thr Thr Ala
1               5                   10                  15

Leu Ile Thr Trp Phe Lys Pro Leu Ala Glu Ile Asp Gly Ile Glu Leu
            20                  25                  30

Thr Tyr Gly Ile Lys Asp Val Pro Gly Asp Arg Thr Thr Ile Asp Leu
        35                  40                  45

Thr Glu Asp Glu Asn Gln Tyr Ser Ile Gly Asn Leu Lys Pro Asp Thr
50                  55                  60

Glu Tyr Glu Val Ser Leu Ile Ser Arg Arg Gly Asp Met Ser Ser Asn
65                  70                  75                  80

Pro Ala Lys Glu Thr Phe Thr Thr
                85

<210> SEQ ID NO 4
<211> LENGTH: 100
<212> TYPE: PRT
<213> ORGANISM: Homo sapiens

<400> SEQUENCE: 4

Thr Gly Leu Asp Ala Pro Arg Asn Leu Arg Arg Val Ser Gln Thr Asp
1               5                   10                  15

Asn Ser Ile Thr Leu Glu Trp Arg Asn Gly Lys Ala Ala Ile Asp Ser
            20                  25                  30

Tyr Arg Ile Lys Tyr Ala Pro Ile Ser Gly Gly Asp His Ala Glu Val
        35                  40                  45

Asp Val Pro Lys Ser Gln Gln Ala Thr Thr Lys Thr Thr Leu Thr Gly
50                  55                  60

Leu Arg Pro Gly Thr Glu Tyr Gly Ile Gly Val Ser Ala Val Lys Glu
65                  70                  75                  80

Asp Lys Glu Ser Asn Pro Ala Thr Ile Asn Ala Ala Thr Glu Leu Asp
                85                  90                  95

Thr Pro Lys Asp
            100

<210> SEQ ID NO 5
<211> LENGTH: 88
<212> TYPE: PRT
<213> ORGANISM: Homo sapiens

<400> SEQUENCE: 5

Asp Thr Pro Lys Asp Leu Gln Val Ser Glu Thr Ala Glu Thr Ser Leu
1               5                   10                  15

Thr Leu Leu Trp Lys Thr Pro Leu Ala Lys Phe Asp Arg Tyr Arg Leu
            20                  25                  30

Asn Tyr Ser Leu Pro Thr Gly Gln Trp Val Gly Val Gln Leu Pro Arg
        35                  40                  45

Asn Thr Thr Ser Tyr Val Leu Arg Gly Leu Glu Pro Gly Gln Glu Tyr
50                  55                  60

Asn Val Leu Leu Thr Ala Glu Lys Gly Arg His Lys Ser Lys Pro Ala
65                  70                  75                  80

Lys Ser Lys Pro Ala Arg Val Lys
                85

<210> SEQ ID NO 6
<211> LENGTH: 92
<212> TYPE: PRT
<213> ORGANISM: Homo sapiens

<400> SEQUENCE: 6

Gln Ala Pro Glu Leu Glu Asn Leu Thr Val Thr Glu Val Gly Trp Asp
1               5                   10                  15

Gly Leu Arg Leu Asn Trp Thr Ala Ala Asp Gln Ala Tyr Glu His Phe
            20                  25                  30

Ile Ile Gln Val Gln Glu Ala Asn Lys Val Glu Ala Ala Arg Asn Leu
        35                  40                  45

Thr Val Pro Gly Ser Leu Arg Ala Val Asp Ile Pro Gly Leu Lys Ala
    50                  55                  60

Ala Thr Pro Tyr Thr Val Ser Ile Tyr Gly Val Ile Gln Gly Tyr Arg
65                  70                  75                  80

Thr Pro Val Leu Ser Ala Glu Ala Ser Thr Gly Glu
                85                  90

<210> SEQ ID NO 7
<211> LENGTH: 91
<212> TYPE: PRT
<213> ORGANISM: Homo sapiens

<400> SEQUENCE: 7

Glu Thr Pro Asn Leu Gly Glu Val Val Ala Glu Val Gly Trp Asp
1               5                   10              15

Ala Leu Lys Leu Asn Trp Thr Ala Pro Glu Gly Ala Tyr Glu Tyr Phe
            20                  25                  30

Phe Ile Gln Val Gln Glu Ala Asp Thr Val Glu Ala Ala Gln Asn Leu
        35                  40                  45

Thr Val Pro Gly Gly Leu Arg Ser Thr Asp Leu Pro Gly Leu Lys Ala
    50                  55                  60

Ala Thr His Tyr Thr Ile Thr Ile Arg Gly Val Thr Gln Asp Phe Ser
65                  70                  75                  80

Thr Thr Pro Leu Ser Val Glu Val Leu Thr Glu
                85                  90

<210> SEQ ID NO 8
<211> LENGTH: 91
<212> TYPE: PRT
<213> ORGANISM: Homo sapiens

<400> SEQUENCE: 8

Glu Val Pro Asp Met Gly Asn Leu Thr Val Thr Glu Val Ser Trp Asp
1               5                   10                  15

Ala Leu Arg Leu Asn Trp Thr Thr Pro Asp Gly Thr Tyr Asp Gln Phe
            20                  25                  30

Thr Ile Gln Val Gln Glu Ala Asp Gln Val Glu Glu Ala His Asn Leu
        35                  40                  45

Thr Val Pro Gly Ser Leu Arg Ser Met Glu Ile Pro Gly Leu Arg Ala
    50                  55                  60

Gly Thr Pro Tyr Thr Val Thr Leu His Gly Glu Val Arg Gly His Ser
65                  70                  75                  80

Thr Arg Pro Leu Ala Val Glu Val Val Thr Glu
                85                  90

<210> SEQ ID NO 9
<211> LENGTH: 95
<212> TYPE: PRT
<213> ORGANISM: Homo sapiens

<400> SEQUENCE: 9

```
Asp Leu Pro Gln Leu Gly Asp Leu Ala Val Ser Glu Val Trp Asp
 1               5                  10                  15

Gly Leu Arg Leu Asn Trp Thr Ala Ala Asp Asn Ala Tyr Glu His Phe
             20                  25                  30

Val Ile Gln Val Gln Glu Val Asn Lys Val Glu Ala Ala Gln Asn Leu
             35                  40                  45

Thr Leu Pro Gly Ser Leu Arg Ala Val Asp Ile Pro Gly Leu Glu Ala
         50                  55                  60

Ala Thr Pro Tyr Arg Val Ser Ile Tyr Gly Val Ile Arg Gly Tyr Arg
 65                  70                  75                  80

Thr Pro Val Leu Ser Ala Glu Ala Ser Thr Ala Lys Glu Pro Glu
                 85                  90                  95
```

<210> SEQ ID NO 10
<211> LENGTH: 91
<212> TYPE: PRT
<213> ORGANISM: Homo sapiens

<400> SEQUENCE: 10

```
Lys Glu Pro Glu Ile Gly Asn Leu Asn Val Ser Asp Ile Thr Pro Glu
 1               5                  10                  15

Ser Phe Asn Leu Ser Trp Met Ala Thr Asp Gly Ile Phe Glu Thr Phe
             20                  25                  30

Thr Ile Glu Ile Ile Asp Ser Asn Arg Leu Leu Glu Thr Val Glu Tyr
             35                  40                  45

Asn Ile Ser Gly Ala Glu Arg Thr Ala His Ile Ser Gly Leu Pro Pro
 50                  55                  60

Ser Thr Asp Phe Ile Val Tyr Leu Ser Gly Leu Ala Pro Ser Ile Arg
 65                  70                  75                  80

Thr Lys Thr Ile Ser Ala Thr Ala Thr Thr Glu
                 85                  90
```

<210> SEQ ID NO 11
<211> LENGTH: 91
<212> TYPE: PRT
<213> ORGANISM: Homo sapiens

<400> SEQUENCE: 11

```
Ala Leu Pro Leu Leu Glu Asn Leu Thr Ile Ser Asp Ile Asn Pro Tyr
 1               5                  10                  15

Gly Phe Thr Val Ser Trp Met Ala Ser Glu Asn Ala Phe Asp Ser Phe
             20                  25                  30

Leu Val Thr Val Val Asp Ser Gly Lys Leu Leu Asp Pro Gln Glu Phe
             35                  40                  45

Thr Leu Ser Gly Thr Gln Arg Lys Leu Glu Leu Arg Gly Leu Ile Thr
 50                  55                  60

Gly Ile Gly Tyr Glu Val Met Val Ser Gly Phe Thr Gln Gly His Gln
 65                  70                  75                  80

Thr Lys Pro Leu Arg Ala Glu Ile Val Thr Glu
                 85                  90
```

<210> SEQ ID NO 12
<211> LENGTH: 92
<212> TYPE: PRT
<213> ORGANISM: Homo sapiens

<400> SEQUENCE: 12

Ala Glu Pro Glu Val Asp Asn Leu Leu Val Ser Asp Ala Thr Pro Asp

```
                1               5                   10                  15
Gly Phe Arg Leu Ser Trp Thr Ala Asp Glu Gly Val Phe Asp Asn Phe
            20                  25                  30

Val Leu Lys Ile Arg Asp Thr Lys Lys Gln Ser Glu Pro Leu Glu Ile
            35                  40                  45

Thr Leu Leu Ala Pro Glu Arg Thr Arg Asp Leu Thr Gly Leu Arg Glu
            50                  55                  60

Ala Thr Glu Tyr Glu Ile Glu Leu Tyr Gly Ile Ser Lys Gly Arg Arg
65                  70                  75                  80

Ser Gln Thr Val Ser Ala Ile Ala Thr Ala Met
                    85                  90

<210> SEQ ID NO 13
<211> LENGTH: 89
<212> TYPE: PRT
<213> ORGANISM: Homo sapiens

<400> SEQUENCE: 13

Gly Ser Pro Lys Glu Val Ile Phe Ser Asp Ile Thr Glu Asn Ser Ala
1               5                   10                  15

Thr Val Ser Trp Arg Ala Pro Thr Ala Gln Val Glu Ser Phe Arg Ile
            20                  25                  30

Thr Tyr Val Pro Ile Thr Gly Gly Thr Pro Ser Met Val Thr Val Asp
            35                  40                  45

Gly Thr Lys Thr Gln Thr Arg Leu Val Lys Leu Ile Pro Gly Val Glu
            50                  55                  60

Tyr Leu Val Ser Ile Ile Ala Met Lys Gly Phe Glu Glu Ser Glu Pro
65                  70                  75                  80

Val Ser Gly Ser Phe Thr Thr Ala Leu
                    85

<210> SEQ ID NO 14
<211> LENGTH: 88
<212> TYPE: PRT
<213> ORGANISM: Homo sapiens

<400> SEQUENCE: 14

Asp Gly Pro Ser Gly Leu Val Thr Ala Asn Ile Thr Asp Ser Glu Ala
1               5                   10                  15

Leu Ala Arg Trp Gln Pro Ala Ile Ala Thr Val Asp Ser Tyr Val Ile
            20                  25                  30

Ser Tyr Thr Gly Glu Lys Val Pro Glu Ile Thr Arg Thr Val Ser Gly
            35                  40                  45

Asn Thr Val Glu Tyr Ala Leu Thr Asp Leu Glu Pro Ala Thr Glu Tyr
            50                  55                  60

Thr Leu Arg Ile Phe Ala Glu Lys Gly Pro Gln Lys Ser Ser Thr Ile
65                  70                  75                  80

Thr Ala Lys Phe Thr Thr Asp Leu
                    85

<210> SEQ ID NO 15
<211> LENGTH: 89
<212> TYPE: PRT
<213> ORGANISM: Homo sapiens

<400> SEQUENCE: 15

Asp Ser Pro Arg Asp Leu Thr Ala Thr Glu Val Gln Ser Glu Thr Ala
1               5                   10                  15
```

```
Leu Leu Thr Trp Arg Pro Pro Arg Ala Ser Val Thr Gly Tyr Leu Leu
             20                  25                  30

Val Tyr Glu Ser Val Asp Gly Thr Val Lys Glu Val Ile Val Gly Pro
         35                  40                  45

Asp Thr Thr Ser Tyr Ser Leu Ala Asp Leu Ser Pro Ser Thr His Tyr
 50                  55                  60

Thr Ala Lys Ile Gln Ala Leu Asn Gly Pro Leu Arg Ser Asn Met Ile
 65                  70                  75                  80

Gln Thr Ile Phe Thr Thr Ile Gly Leu
                 85

<210> SEQ ID NO 16
<211> LENGTH: 89
<212> TYPE: PRT
<213> ORGANISM: Artificial Sequence
<220> FEATURE:
<223> OTHER INFORMATION: Binding polypeptide

<400> SEQUENCE: 16

Leu Pro Ala Pro Lys Asn Leu Val Val Ser Glu Val Thr Glu Asp Ser
 1               5                  10                  15

Leu Arg Leu Ser Trp Thr Ala Pro Asp Ala Ala Phe Asp Ser Phe Leu
             20                  25                  30

Ile Gln Tyr Gln Glu Ser Glu Lys Val Gly Glu Ala Ile Asn Leu Thr
         35                  40                  45

Val Pro Gly Ser Glu Arg Ser Tyr Asp Leu Thr Gly Leu Lys Pro Gly
     50                  55                  60

Thr Glu Tyr Thr Val Ser Ile Tyr Gly Val Lys Gly Gly His Arg Ser
 65                  70                  75                  80

Asn Pro Leu Ser Ala Glu Phe Thr Thr
                 85

<210> SEQ ID NO 17
<211> LENGTH: 267
<212> TYPE: DNA
<213> ORGANISM: Artificial Sequence
<220> FEATURE:
<223> OTHER INFORMATION: Nucleotide encoding binding polynucleotide

<400> SEQUENCE: 17
ctgccggcgc cgaaaaacct ggttgtttct gaagttaccg aagactctct gcgtctgtct      60
tggaccgcgc cggacgcggc gttcgactct ttcctgatcc agtaccagga atctgaaaaa     120
gttggtgaag cgatcaacct gaccgttccg ggttctgaac gttcttacga cctgaccggt     180
ctgaaaccgg gtaccgaata caccgtttct atctacggtg ttaaaggtgg tcaccgttct     240
aacccgctgt ctgcggaatt caccacc                                         267

<210> SEQ ID NO 18
<211> LENGTH: 68
<212> TYPE: DNA
<213> ORGANISM: Artificial Sequence
<220> FEATURE:
<221> NAME/KEY: unknown
<222> LOCATION: (28)(29)(31)(32)(34)(35)(37)(38)(40)(41)(43)(44)(46)(47)
<223> OTHER INFORMATION: Primer wherein n can be represented by a, c, t
      or g

<400> SEQUENCE: 18
gaatacaccg tttctatcta cggtgttnns nnsnnsnnsn nsnnsnnscc gctgtctgcg      60
gaattcac                                                              68
```

-continued

```
<210> SEQ ID NO 19
<211> LENGTH: 64
<212> TYPE: DNA
<213> ORGANISM: Artificial Sequence
<220> FEATURE:
<221> NAME/KEY: unknown
<222> LOCATION: (22)(23)(25)(26)(28)(29)(31)(32)(34)(35)(37)(38)
<223> OTHER INFORMATION: Primer wherein n can be represented by a, c, t
      or g

<400> SEQUENCE: 19
gactctctgc gtctgtcttg gnnsnnsnns nnsnnsnnst tcgactcttt cctgatccag    60
tacc                                                                64

<210> SEQ ID NO 20
<211> LENGTH: 63
<212> TYPE: DNA
<213> ORGANISM: Artificial Sequence
<220> FEATURE:
<221> NAME/KEY: unknown
<222> LOCATION: (21)(22)(23)(24)(25)(26)(27)(28)(29)(30)(31)(32)(33)
      (34)(35)(36)(37)(38)(39)(40)(41)
<223> OTHER INFORMATION: Primer wherein n can be represented by a, c, t
      or g and s can be represented by g or c.

<400> SEQUENCE: 20
gtgaattccg cagacagcgg snnsnnsnns nnsnnsnnsn naacaccgta gatagaaacg    60
gtg                                                                 63

<210> SEQ ID NO 21
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 21

Ser Tyr Gly Phe Asn Asn
 1               5

<210> SEQ ID NO 22
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 22

Thr Tyr Glu Gly Glu Ser
 1               5

<210> SEQ ID NO 23
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 23

Thr Tyr Glu Ser Glu Ser
 1               5

<210> SEQ ID NO 24
<211> LENGTH: 6
```

```
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 24

Thr Asn Trp Met Asp Ser
1               5

<210> SEQ ID NO 25
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 25

Lys Ser Val Phe Ile Met
1               5

<210> SEQ ID NO 26
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 26

Tyr Ser Ser Tyr Ala Thr
1               5

<210> SEQ ID NO 27
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 27

Arg Phe His Pro Phe Pro
1               5

<210> SEQ ID NO 28
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 28

Met Met Cys Met Pro Leu
1               5

<210> SEQ ID NO 29
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 29

Tyr Cys Arg Val Arg Asp
1               5
```

<210> SEQ ID NO 30
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 30

Met Asp Cys Phe Met Gly
 1               5

<210> SEQ ID NO 31
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 31

Thr Tyr Arg Phe Asn Ser
 1               5

<210> SEQ ID NO 32
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 32

Ala Ser Arg Arg Ser Leu
 1               5

<210> SEQ ID NO 33
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 33

Thr Ile Glu Ser Glu Ser
 1               5

<210> SEQ ID NO 34
<211> LENGTH: 5
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 34

Thr Leu Met Gln Ser
 1               5

<210> SEQ ID NO 35
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

```
<400> SEQUENCE: 35

Ile Tyr Asp Ser Glu Ser
1               5

<210> SEQ ID NO 36
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 36

Asp Arg Lys Arg Phe Ile
1               5

<210> SEQ ID NO 37
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 37

Glu Phe Trp Arg Gly Ser
1               5

<210> SEQ ID NO 38
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 38

Gly Leu Leu Asp Pro Leu
1               5

<210> SEQ ID NO 39
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 39

Gly Leu Val Leu Pro Glu
1               5

<210> SEQ ID NO 40
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 40

Met Ala Ser Asp Gly Leu
1               5

<210> SEQ ID NO 41
<211> LENGTH: 6
<212> TYPE: PRT
<213> ORGANISM: Artificial Sequence
```

```
<220> FEATURE:
<223> OTHER INFORMATION: Protein Scaffold Based On A Human Fibronectin
      Type III (FN3) Domain Sequence

<400> SEQUENCE: 41

Asn Lys Thr Glu Thr Asn
1               5

<210> SEQ ID NO 42
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 42

Gln Ala Glu Arg Lys Val
1               5

<210> SEQ ID NO 43
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 43

Ser Gln Val Cys Thr Leu
1               5

<210> SEQ ID NO 44
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 44

Tyr Phe Asp Lys Asp Ser
1               5

<210> SEQ ID NO 45
<211> LENGTH: 6
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 45

Tyr Phe Glu Cys Glu Pro
1               5

<210> SEQ ID NO 46
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 46

Gln Ile Gly Pro Ile Ile Pro
1               5
```

```
<210> SEQ ID NO 47
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 47

Ser Ile Arg Thr Ile Asp Ser
1               5

<210> SEQ ID NO 48
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 48

Pro Lys Phe His Ser Pro Leu
1               5

<210> SEQ ID NO 49
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 49

Trp Lys Thr Thr Ile Trp Phe
1               5

<210> SEQ ID NO 50
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 50

Arg Lys Asn Trp Lys Thr Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 51

Arg Leu Phe Arg Ile Tyr Gln
1               5

<210> SEQ ID NO 52
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 52
```

Trp Leu Ser Arg Ser Tyr Asp
1               5

<210> SEQ ID NO 53
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 53

Trp Leu Ser Arg Ser Cys Asp
1               5

<210> SEQ ID NO 54
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 54

Trp Met Gly Pro Tyr Cys Asp
1               5

<210> SEQ ID NO 55
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 55

Arg Arg Arg Arg Tyr Ser Phe
1               5

<210> SEQ ID NO 56
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 56

His Ile Val Pro Met Val Pro
1               5

<210> SEQ ID NO 57
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 57

Gln Ile Glu Pro Ile Ile Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Protein Scaffold Based On A Human Fibronectin Type III (FN3) Domain Sequence

<400> SEQUENCE: 58

Pro Ser Ala Ala Asn Asn Pro
1               5

<210> SEQ ID NO 59
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 59

Val Arg Leu Arg Tyr Val Gln
1               5

<210> SEQ ID NO 60
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 60

Gln Val Gly Pro Leu Ile Pro
1               5

<210> SEQ ID NO 61
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 61

Arg Ile Gly Pro Ile Leu Pro
1               5

<210> SEQ ID NO 62
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 62

Gln Ile Gly Pro Leu Leu Pro
1               5

<210> SEQ ID NO 63
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 63

Arg Ile Gly Pro Leu Leu Pro
1               5

<210> SEQ ID NO 64
<211> LENGTH: 7

```
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 64

Gln Val Gly Pro Leu Leu Pro
 1               5

<210> SEQ ID NO 65
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 65

Arg Ile Gly Pro Met Leu Pro
 1               5

<210> SEQ ID NO 66
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 66

Gln Ile Gly Pro Val Leu Pro
 1               5

<210> SEQ ID NO 67
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 67

Arg Ile Gly Pro Val Leu Pro
 1               5

<210> SEQ ID NO 68
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 68

Gln Ile Gly Pro Met Met Pro
 1               5

<210> SEQ ID NO 69
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 69

Gln Val Gly Pro Leu Val Pro
 1               5
```

```
<210> SEQ ID NO 70
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 70

Gln Ile Gly Pro Met Leu Pro
 1               5

<210> SEQ ID NO 71
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 71

Gln Val Gly Pro Ile Leu Pro
 1               5

<210> SEQ ID NO 72
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 72

Gln Val Gly Pro Met Leu Pro
 1               5

<210> SEQ ID NO 73
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 73

Gln Ile Gly Pro Ile Val Pro
 1               5

<210> SEQ ID NO 74
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 74

Met Ile Gly Pro Leu Leu Pro
 1               5

<210> SEQ ID NO 75
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence
```

```
<400> SEQUENCE: 75

Gln Ile Gly Pro Leu Phe Pro
1               5

<210> SEQ ID NO 76
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 76

Gln Ile Gly Pro Met Val Pro
1               5

<210> SEQ ID NO 77
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 77

Gln Ile Gly Pro Ile Val Pro
1               5

<210> SEQ ID NO 78
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 78

Arg Ile Glu Pro Ile Leu Pro
1               5

<210> SEQ ID NO 79
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 79

Val Ala Gly Ser Val Trp Pro
1               5

<210> SEQ ID NO 80
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 80

Arg Glu Gly Ala Thr Leu Tyr
1               5

<210> SEQ ID NO 81
<211> LENGTH: 7
<212> TYPE: PRT
<213> ORGANISM: Artificial Sequence
```

```
<220> FEATURE:
<223> OTHER INFORMATION: Protein Scaffold Based On A Human Fibronectin
      Type III (FN3) Domain Sequence

<400> SEQUENCE: 81

Lys Gln Ile Pro Pro Ile Leu
 1               5

<210> SEQ ID NO 82
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 82

Leu Ser Leu Ser Ser Val Leu
 1               5

<210> SEQ ID NO 83
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 83

His Met Leu Leu Pro Leu Pro
 1               5

<210> SEQ ID NO 84
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 84

Met Ile Gly Pro Leu Ile Pro
 1               5

<210> SEQ ID NO 85
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 85

Thr Ile Gly Pro His Ile Pro
 1               5

<210> SEQ ID NO 86
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 86

Glu Ile Gly Pro Cys Leu Pro
 1               5
```

```
<210> SEQ ID NO 87
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 87

Glu Ile Gly Pro Val Leu Pro
1               5

<210> SEQ ID NO 88
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 88

Lys Ile Gly Pro Cys Leu Pro
1               5

<210> SEQ ID NO 89
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 89

Met Ile Gly Pro Val Leu Pro
1               5

<210> SEQ ID NO 90
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 90

Gln Ile Gly Pro Ile Leu Pro
1               5

<210> SEQ ID NO 91
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 91

Glu Val Gly Pro Ile Leu Pro
1               5

<210> SEQ ID NO 92
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 92
```

Gln Val Gly Pro Leu Leu Pro
1               5

<210> SEQ ID NO 93
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 93

Gln Ile Gly Pro Val Met Pro
1               5

<210> SEQ ID NO 94
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 94

Gln Ile Gly Pro Cys Val Pro
1               5

<210> SEQ ID NO 95
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 95

Gln Ile Gly Pro Leu Val Pro
1               5

<210> SEQ ID NO 96
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 96

Arg Gly Leu Val Met Pro Met
1               5

<210> SEQ ID NO 97
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 97

Met Ile Gly Pro Ile Leu Pro
1               5

<210> SEQ ID NO 98
<211> LENGTH: 7
<212> TYPE: PRT
<213> ORGANISM: Artificial Sequence
<220> FEATURE:
<223> OTHER INFORMATION: Protein Scaffold Based On A Human Fibronectin Type III (FN3) Domain Sequence

<400> SEQUENCE: 98

Cys Ile Gly Pro Met Val Pro
1               5

<210> SEQ ID NO 99
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 99

Phe Ile Gly Pro Val Leu Pro
1               5

<210> SEQ ID NO 100
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 100

His Ile Gly Pro Ile Leu Pro
1               5

<210> SEQ ID NO 101
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 101

His Ile Gly Pro Ile Met Pro
1               5

<210> SEQ ID NO 102
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 102

His Ile Gly Pro Tyr Leu Pro
1               5

<210> SEQ ID NO 103
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 103

His Val Gly Pro Ile Leu Pro
1               5

<210> SEQ ID NO 104
<211> LENGTH: 7

```
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 104

Ile Ile Gly Pro Leu Leu Pro
1               5

<210> SEQ ID NO 105
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 105

Met Val Gly Pro Leu Leu Pro
1               5

<210> SEQ ID NO 106
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 106

Met Val Gly Pro Leu Leu Pro
1               5

<210> SEQ ID NO 107
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 107

Asn Ile Gly Pro Tyr Leu Pro
1               5

<210> SEQ ID NO 108
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 108

Asn Ile Gly Pro Tyr Leu Pro
1               5

<210> SEQ ID NO 109
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 109

Gln Ile Gly Pro His Leu Pro
1               5
```

<210> SEQ ID NO 110
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 110

Gln Ile Gly Pro Ile Leu Gly
 1               5

<210> SEQ ID NO 111
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 111

Gln Ile Gly Pro Ile Leu Ser
 1               5

<210> SEQ ID NO 112
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 112

Gln Ile Gly Pro Ile Leu Thr
 1               5

<210> SEQ ID NO 113
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 113

Gln Ile Gly Pro Ile Met Pro
 1               5

<210> SEQ ID NO 114
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 114

Gln Ile Gly Pro Ile Pro Ile
 1               5

<210> SEQ ID NO 115
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

```
<400> SEQUENCE: 115

Gln Ile Gly Pro Leu Leu Asn
1               5

<210> SEQ ID NO 116
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 116

Gln Ile Gly Pro Val Phe Pro
1               5

<210> SEQ ID NO 117
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 117

Gln Ile Gly Pro Val Leu Ser
1               5

<210> SEQ ID NO 118
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 118

Gln Ile Gly Pro Trp Leu Pro
1               5

<210> SEQ ID NO 119
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 119

Gln Val Gly Pro Ile Met Asn
1               5

<210> SEQ ID NO 120
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 120

Gln Val Gly Pro Ile Met Pro
1               5

<210> SEQ ID NO 121
<211> LENGTH: 7
<212> TYPE: PRT
<213> ORGANISM: Artificial Sequence
```

```
<220> FEATURE:
<223> OTHER INFORMATION: Protein Scaffold Based On A Human Fibronectin
      Type III (FN3) Domain Sequence

<400> SEQUENCE: 121

Gln Val Gly Pro Ile Val Pro
  1               5

<210> SEQ ID NO 122
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 122

Gln Val Gly Pro Leu Leu Ser
  1               5

<210> SEQ ID NO 123
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 123

Gln Val Gly Pro Val Leu Pro
  1               5

<210> SEQ ID NO 124
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 124

Gln Val Gly Pro Val Leu Pro
  1               5

<210> SEQ ID NO 125
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 125

Arg Ile Gly Pro Ile Met Pro
  1               5

<210> SEQ ID NO 126
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 126

Arg Ile Gly Pro Ile Val Pro
  1               5
```

```
<210> SEQ ID NO 127
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 127

Arg Ile Gly Pro Met Phe Pro
1               5

<210> SEQ ID NO 128
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 128

Arg Ile Gly Pro Met Ile Pro
1               5

<210> SEQ ID NO 129
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 129

Arg Ile Gly Pro Met Val Pro
1               5

<210> SEQ ID NO 130
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 130

Arg Ile Gly Pro Val Ile Pro
1               5

<210> SEQ ID NO 131
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 131

Arg Val Gly Pro Ile Leu Pro
1               5

<210> SEQ ID NO 132
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 132
```

Arg Val Gly Pro Leu Leu Pro
1               5

<210> SEQ ID NO 133
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 133

Thr Val Gly Pro His Ile Pro
1               5

<210> SEQ ID NO 134
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 134

Pro Ser Trp Arg Ser Asn Trp
1               5

<210> SEQ ID NO 135
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 135

Ala Leu Arg Ala Thr Leu Glu
1               5

<210> SEQ ID NO 136
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 136

Lys Tyr Gly Tyr Leu Thr Pro
1               5

<210> SEQ ID NO 137
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 137

Arg Ile Gly Pro Met Leu Pro
1               5

<210> SEQ ID NO 138
<211> LENGTH: 7
<212> TYPE: PRT
<213> ORGANISM: Artificial Sequence
<220> FEATURE:
<223> OTHER INFORMATION: Protein Scaffold Based On A Human Fibronectin -continued Type III (FN3) Domain Sequence

<400> SEQUENCE: 138

Asn Pro Phe Cys Ser Arg Phe
1               5

<210> SEQ ID NO 139
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 139

Tyr Tyr Leu His Gln Trp Cys
1               5

<210> SEQ ID NO 140
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 140

His Ile Val Pro Leu Leu Arg
1               5

<210> SEQ ID NO 141
<211> LENGTH: 7
<212> TYPE: PRT
<213> ORGANISM: Artificial Sequence
<220> FEATURE:
<223> OTHER INFORMATION: Protein Scaffold Based On A Human Fibronectin
      Type III (FN3) Domain Sequence

<400> SEQUENCE: 141

Thr Ser Gly Gly Gly Gly Ser
1               5